US008293905B2

(12) United States Patent
Asaumi et al.

(10) Patent No.: US 8,293,905 B2
(45) Date of Patent: Oct. 23, 2012

(54) BIPYRIDINE COMPOUND, TRANSITION METAL COMPLEX, AND METHOD FOR PRODUCTION OF CONJUGATED AROMATIC COMPOUND USING THE TRANSITION METAL COMPLEX

(75) Inventors: Taku Asaumi, Kobe (JP); Takashi Kamikawa, Nara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 376 days.

(21) Appl. No.: 12/664,960

(22) PCT Filed: Jun. 18, 2008

(86) PCT No.: PCT/JP2008/061503
§ 371 (c)(1), (2), (4) Date: Dec. 16, 2009

(87) PCT Pub. No.: WO2008/156196
PCT Pub. Date: Dec. 24, 2008

(65) Prior Publication Data
US 2010/0184978 A1    Jul. 22, 2010

(30) Foreign Application Priority Data

Jun. 20, 2007 (JP) .................................. 2007-162260

(51) Int. Cl.
*C07F 7/02* (2006.01)
*C07D 213/22* (2006.01)
(52) U.S. Cl. ........................... 546/14; 546/257; 546/260
(58) Field of Classification Search .................... 546/14, 546/257, 260
See application file for complete search history.

(56) References Cited

U.S. PATENT DOCUMENTS 6,310,231 B1 * 10/2001 Igarashi et al. ................ 556/489
2006/0058524 A1    3/2006 Falcou et al.

FOREIGN PATENT DOCUMENTS

| EP | 2 128 165 A1 | 12/2009 |
|----|--------------|---------|
| JP | 59-176317 A  | 10/1984 |

OTHER PUBLICATIONS

Nishimura et al. Tetrahedron Letters, 39 (1998), pp. 4359-4362/.*
European Search Report, dated Jul. 28, 2011, 4 pages.

The Notification and International Preliminary Report on Patentability and Translation of the Written Opinion received in the corresponding International Application PCT/JP2008/061503. (6 pgs.), Jan. 12, 2010.
The International Search Report received in the correspondence International Patent Application No. PCT/JP2008/061503, dated Jul. 22, 2008.
Danishefsky, et al., "Selective Carbon-Carbon Bond Formation via Transition Metal Catalysis. 3.[1] A Highly Selective Synthesis of Unsymmetrical Biaryls and Diarylmethanee by the Nickel-or Palladium-Catalyzed Reaction of Aryl-and Benzylzinc Derivatives with Aryl Halides", *J. Org. Chem.* vol. 42, No. 10, 1977, pp. 1821-1823.
Hagberg, et al., "Advances in N1(0)-Catalyzed Coupling for the Synthesis of Polythiophenes and Polyphenylenes", *Macromolecules*, vol. 37, 2004, pp. 4748-4754.
Stange, et al., "Ruthenium and rhenium complexes with silyl-substituted bipyridyl ligands", *Journal of Organometallic Chemistry*, vol. 612, 2000, pp. 117-124.
Trecourt, et al., "First Synthesis of Caerulomycin C", *J. Org. Chem.*, vol. 61, 1996, pp. 1673-1676.
Yamamoto, et al., "Preparation of π-Conjugated Poly(thiophene-2,5-diyl), Poly(p-phenylene), and Related Polymers Using Zerovalent Nickel Complexes. Linear Structure and Properties of the π-Conjugated Polymers", *Macromolecules*, vol. 25, 1992, pp. 1214-1223.

\* cited by examiner

*Primary Examiner* — Joseph K. McKane
*Assistant Examiner* — Samantha Shterengarts
(74) *Attorney, Agent, or Firm* — Foley & Lardner LLP

(57) ABSTRACT

A bipyridine compound represented by the formula (1):

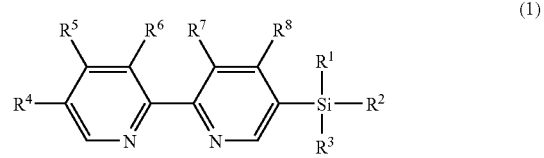

wherein $R^1$, $R^2$ and $R^3$ each independently represent a C1-C10 alkyl group which may be substituted etc., and $R^4$, $R^5$, $R^6$, $R^7$ and $R^8$ each independently represent a hydrogen atom etc., a transition metal complex obtained by contacting a bipyridine compound represented by the formula (1) with a compound of a transition metal belonging to Group 9, 10 or 11, and a method for production of a conjugated aromatic compound comprising reacting an aromatic compound (A) wherein one or two leaving groups are bonded to an aromatic ring with an aromatic compound (A) having the same structure as that of the above-mentioned aromatic compound (A) or an aromatic compound (B) being structurally different from the above-mentioned aromatic compound (A) and having one or two leaving groups bonded to an aromatic ring, in the presence of the transition metal complex.

21 Claims, No Drawings

BIPYRIDINE COMPOUND, TRANSITION METAL COMPLEX, AND METHOD FOR PRODUCTION OF CONJUGATED AROMATIC COMPOUND USING THE TRANSITION METAL COMPLEX

TECHNICAL FIELD

The present invention relates to a bipyridine compound, a transition metal complex and a method for production of a conjugated aromatic compound using the transition metal complex.

BACKGROUND ART

It has been known that bipyridine compounds form a complex by coordination to various transition metals, and that the complex acts as a catalyst in various organic reactions. As the organic reaction using the complex, Macromolecules, 1992, 25, 1214-1223 discloses a coupling reaction of aromatic dihalide compounds.

DISCLOSURE OF THE INVENTION

The present invention provides:

<1> A bipyridine compound represented by the formula (1):

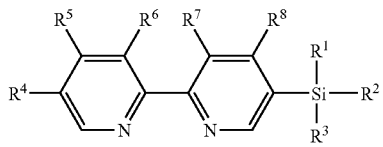

wherein $R^1$, $R^2$ and $R^3$ each independently represent a C1-C10 alkyl group which may be substituted, a C1-C5 alkoxy group which may be substituted or a C6-C10 aryl group which may be substituted, and $R^4$, $R^5$, $R^6$, $R^7$ and $R^8$ each independently represent a hydrogen atom or a C1-C3 alkyl group which may be substituted (hereinafter, sometimes simply referred to as the bipyridine compound (1));

<2> The bipyridine compound according to <1>, wherein $R^1$, $R^2$ and $R^3$ each independently represent a methyl group, an ethyl group, an n-propyl group, an isopropyl group, a tert-butyl group, a cyclohexyl group, a benzyl group, a phenyl group, a 4-methylphenyl group, a methoxy group or an ethoxy group;

<3> The bipyridine compound according to <1>, wherein $R^1$, $R^2$ and $R^3$ are methyl groups;

<4> The bipyridine compound according to <1>, wherein $R^1$ is a methyl group, and $R^2$ and $R^3$ are phenyl groups;

<5> The bipyridine compound according to <1>, wherein $R^1$ and $R^2$ are methyl groups and $R^3$ is a phenyl group;

<6> The bipyridine compound according to <1>, wherein $R^1$ and $R^2$ are methyl groups and $R^3$ is a cyclohexyl group;

<7> The bipyridine compound according to <1>, wherein $R^1$ and $R^2$ are methyl groups and $R^3$ is a tert-butyl group;

<8> The bipyridine compound according to <1>, wherein $R^1$, $R^2$ and $R^3$ are phenyl groups;

<9> The bipyridine compound according to any of <1> to <8>, wherein $R^4$, $R^5$, $R^6$, $R^7$ and $R^8$ are hydrogen atoms;

<10> A transition metal complex obtained by contacting a bipyridine compound represented by the formula (1):

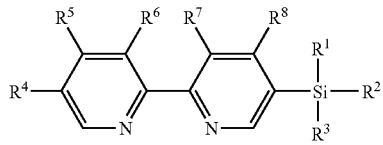

wherein $R^1$, $R^2$ and $R^3$ each independently represent a C1-C10 alkyl group which may be substituted, a C1-C5 alkoxy group which may be substituted or a C6-C10 aryl group which may be substituted, and $R^4$, $R^5$, $R^6$, $R^7$ and $R^8$ each independently represent a hydrogen atom or a C1-C3 alkyl group which may be substituted, with a compound of a transition metal belonging to Group 9, 10 or 11;

<11> The transition metal complex according to <10>, which is obtained by contacting the bipyridine compound represented by the formula (1) with a compound of a transition metal belonging to Group 10;

<12> The transition metal complex according to <11>, wherein the compound of a transition metal belonging to Group 10 is a nickel compound;

<13> The transition metal complex according to any of <10> to <12>, wherein $R^1$, $R^2$ and $R^3$ each independently represent a methyl group, an ethyl group, an n-propyl group, an isopropyl group, a tert-butyl group, a cyclohexyl group, a benzyl group, a phenyl group, a 4-methylphenyl group, a methoxy group or an ethoxy group;

<14> The transition metal complex according to any of <10> to <12>, wherein $R^1$, $R^2$ and $R^3$ are methyl groups;

<15> The transition metal complex according to any of <10> to <12>, wherein $R^1$ is a methyl group and $R^2$ and $R^3$ are phenyl groups;

<16> The transition metal complex according to any of <10> to <12>, wherein $R^1$ and $R^2$ are methyl groups and $R^3$ is a phenyl group;

<17> The transition metal complex according to any of <10> to <12>, wherein $R^1$ and $R^2$ are methyl groups and $R^3$ is a cyclohexyl group;

<18> The transition metal complex according to any of <10> to <12>, wherein $R^1$ and $R^2$ are methyl groups and $R^3$ is a tert-butyl group;

<19> The transition metal complex according to any of <10> to <12>, wherein $R^1$, $R^2$ and $R^3$ are phenyl groups;

<20> The transition metal complex according to any of <10> to <19>, wherein $R^4$, $R^5$, $R^6$, $R^7$ and $R^8$ are hydrogen atoms;

<21> A method for production of a bipyridine compound represented by the formula (1):

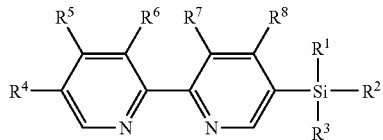

wherein $R^1$, $R^2$ and $R^3$ each independently represent a C1-C10 alkyl group which may be substituted, a C1-C5 alkoxy group which may be substituted or a C6-C10 aryl group which may be substituted, and $R^4$, $R^5$, $R^6$, $R^7$ and $R^8$ each independently represent a hydrogen atom or a C1-C3 alkyl group which may be substituted, which comprises reacting a pyridine compound represented by the formula (2):

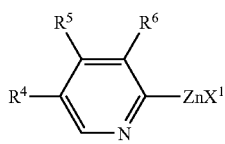
(2)

wherein $R^4$, $R^5$ and $R^6$ are the same as defined above, and $X^1$ represents a halogen atom, with a pyridine compound represented by the formula (3):

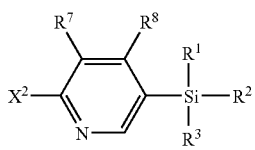
(3)

wherein $R^1$, $R^2$, $R^3$, $R^7$ and $R^8$ are the same as defined above, and $X^2$ represents a halogen atom, a trifluoromethanesulfonyloxy group, a p-toluenesulfonyloxy group or a methanesulfonyloxy group, in the presence of a palladium catalyst;

<22> A method for production of a conjugated aromatic compound comprising reacting an aromatic compound (A) wherein one or two leaving groups are bonded to an aromatic ring with an aromatic compound (A) having the same structure as that of the above-mentioned aromatic compound (A) or an aromatic compound (B) being structurally different from the above-mentioned aromatic compound (A) and having one or two leaving groups bonded to an aromatic ring, in the presence of a transition metal complex obtained by contacting a bipyridine compound represented by the formula (1):

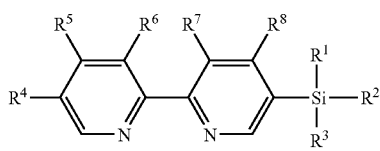
(1)

wherein $R^1$, $R^2$ and $R^3$ each independently represent a C1-C10 alkyl group which may be substituted, a C1-C5 alkoxy group which may be substituted or a C6-C10 aryl group which may be substituted, and $R^4$, $R^5$, $R^6$, $R^7$ and $R^8$ each independently represent a hydrogen atom or a C1-C3 alkyl group which may be substituted, with a compound of a transition metal belonging to Group 9, 10 or 11;

<23> The method for production according to <22>, wherein the aromatic rings of the aromatic compounds (A) and (B) are independently a benzene ring, a biphenyl ring, a naphthalene ring, a fluorene ring, an anthracene ring, a phenanthrene ring, a thiophene ring, a pyrrole ring, a pyridine ring, a pyrimidine ring, a quinoline ring, an isoquinoline ring or a quinoxaline ring, and the aromatic ring may be substituted with at least one group uninvolved in the reaction;

<24> The method for production according to <22> or <23>, wherein the transition metal complex is a transition metal complex obtained by contacting the bipyridine compound represented by the formula (1) with a compound of a transition metal belonging to Group 10;

<25> The method for production according to <24>, wherein the compound of a transition metal belonging to Group 10 is a nickel compound;

<26> The method for production according to any of <22> to <25>, wherein an aromatic compound (A) is reacted with an aromatic compound (A) having the same structure as that of the aromatic compound (A);

<27> The method for production according to <26>, wherein the aromatic compound (A) is an aromatic compound represented by the formula (4):

$$Ar^1-(X^3)_n \quad (4)$$

wherein $Ar^1$ represents an n-valent aromatic group, and the aromatic ring composed of the above-mentioned aromatic group is a benzene ring, a biphenyl ring, a naphthalene ring, a fluorene ring, an anthracene ring, a phenanthrene ring, a thiophene ring, a pyrrole ring, a pyridine ring, a pyrimidine ring, a quinoline ring, an isoquinoline ring or a quinoxaline ring, and may be substituted with at least one group uninvolved in the reaction, $X^3$ represents a leaving group, n represents 1 or 2, and when n is 2, $X^3$s may be same or different each other;

<28> The method for production according to <26>, wherein the aromatic compound (A) is an aromatic compound represented by the formula (5):

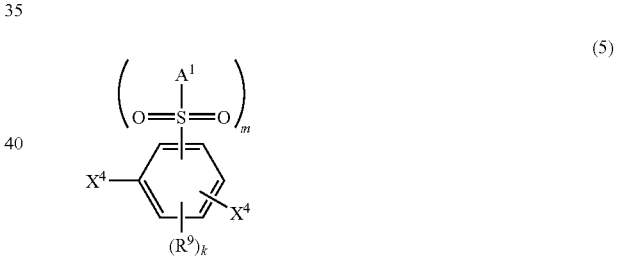
(5)

wherein $A^1$ represents an amino group substituted with one or two hydrocarbon groups wherein sum of carbon atoms of the hydrocarbon groups is 3 to 20, or a C3-C20 alkoxy group, and the above-mentioned hydrocarbon and alkoxy groups may be substituted with at least one group selected from the group consisting of a fluorine atom, a C1-C20 alkoxy group, a C6-C20 aryl group, a C6-C20 aryloxy group, a C2-C20 acyl group and a cyano group, $R^9$ represents a hydrogen atom, a fluorine atom, a C1-C20 alkyl group, a C1-C20 alkoxy group, a C6-C20 aryl group, a C6-C20 aryloxy group, a C2-C20 acyl group or a cyano group, and the above-mentioned C1-C20 alkyl, C1-C20 alkoxy, C6-C20 aryl, C6-C20 aryloxy and C2-C20 acyl groups may be substituted with at least one substituent selected from the group consisting of a fluorine atom, a cyano group, a C1-C20 alkoxy group, a C6-C20 aryl group and a C6-C20 aryloxy group, and when multiple $R^9$s exist, $R^9$s may be the same groups or different groups, and the neighboring two $R^9$s may be bonded to form a ring, $X^4$ represents a chlorine atom, a bromine atom or an iodine atom, and m represents 1 or 2 and k represents 4-m;

<29> The method for production according to <26>, wherein the aromatic compound (A) is an aromatic compound represented by the formula (6):

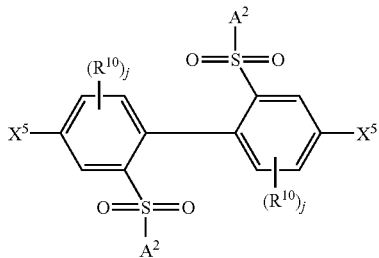

(6)

wherein A² represents an amino group substituted with one or two hydrocarbon groups wherein sum of carbon atoms of the hydrocarbon groups is 3 to 20, or a C3-C20 alkoxy group, and the above-mentioned hydrocarbon and alkoxy groups may be substituted with at least one group selected from the group consisting of a fluorine atom, a C1-C20 alkoxy group, a C6-C20 aryl group, a C6-C20 aryloxy group, a C2-C20 acyl group and a cyano group, R¹⁰ represents a fluorine atom, a C1-C20 alkyl group, a C1-C20 alkoxy group, a C6-C20 aryl group, a C6-C20 aryloxy group, a C2-C20 acyl group or a cyano group, and the above-mentioned C1-C20 alkyl, C1-C20 alkoxy, C6-C20 aryl, C6-C20 aryloxy and C2-C20 acyl groups may be substituted with at least one substituent selected from the group consisting of a fluorine atom, a cyano group, a C1-C20 alkoxy group, a C6-C20 aryl group and a C6-C20 aryloxy group, and when multiple R¹⁰s exist, R¹⁰s may be the same groups or different groups, and the neighboring two R¹⁰s may be bonded to form a ring, X⁵ represents a chlorine atom, a bromine atom or an iodine atom, and j represents an integer of 0 to 3;

<30> The method for production according to any of <22> to <25>, wherein the aromatic compound (A) is reacted with an aromatic compound (B) structurally different from the aromatic compound (A);

<31> The method for production according to <30>, wherein an aromatic compound represented by the formula (4):

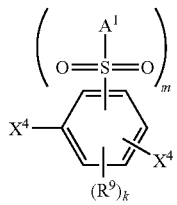

(4)

wherein Ar¹, X³ and n are the same as defined in <27>, is used as the aromatic compound (A), and an aromatic compound represented by the formula (4) and structurally different from the aromatic compound (A), an aromatic compound represented by the formula (5):

(5)

wherein A¹, R⁹, X⁴, m and k are the same as defined in <28>, an aromatic compound represented by the formula (6):

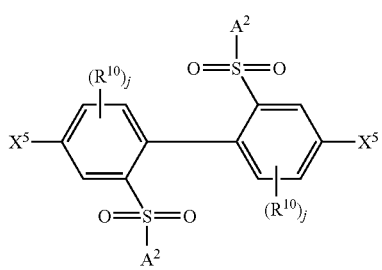

(6)

wherein A², R¹⁰, X⁵ and j are the same as defined in <29>, or an aromatic compound represented by the formula (7):

(7)

wherein a, b and c each independently represent 0 or 1, h represents an integer of 5 or more,
Ar², Ar³, Ar⁴ and Ar⁵ each independently represent a divalent aromatic group, and the divalent aromatic group may be substituted with at least one substituent selected from the group consisting of the following (a2) to (e2):
(a2) a C1-C20 alkyl group which may be substituted with at least one substituent selected from the group consisting of a fluorine atom, a cyano group, a C1-C20 alkoxy group, a C6-C20 aryl group and a C6-C20 aryloxy group;
(b2) a C1-C20 alkoxy group which may be substituted with at least one substituent selected from the group consisting of a fluorine atom, a cyano group, a C1-C20 alkoxy group, a C6-C20 aryl group and a C6-C20 aryloxy group;
(c2) a C6-C20 aryl group which may be substituted with at least one substituent selected from the group consisting of a fluorine atom, a cyano group, a C1-C20 alkoxy group and a C6-C10 aryloxy group;
(d2) a C6-C20 aryloxy group which may be substituted with at least one substituent selected from the group consisting of a fluorine atom, a cyano group, a C1-C20 alkoxy group and a C6-C20 aryloxy group; and (e2) a C2-C20 acyl group which may be substituted with at least one substituent selected from the group consisting of a fluorine atom, a cyano group, a C1-C20 alkoxy group, a C6-C20 aryl group and a C6-C20 aryloxy group, $Y^1$ and $Y^2$ each independently represent a single bond, —CO—, —SO$_2$—, —C(CH$_3$)$_2$—, —C(CF$_3$)$_2$— or a fluorene-9,9-diyl group, $Z^1$ and $Z^2$ each independently represent —O— or —S—, and $X^6$ represents a chlorine atom, a bromine atom or an iodine atom, is used as the aromatic compound (B);

<32> The method for production according to <30>, wherein an aromatic compound represented by the formula (5):

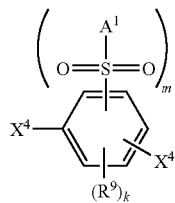

(5)

wherein $A^1$, $R^9$, $X^4$, m and k are the same as defined in <28>, is used as the aromatic compound (A), and an aromatic compound represented by the formula (5) and structurally different from the aromatic compound (A) or an aromatic compound represented by the formula (7):

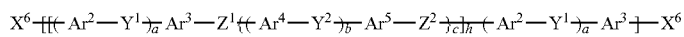

(7)

wherein a, b, c, h, $Ar^2$, $Ar^3$, $Ar^4$, $Ar^5$, $Y^1$, $Y^2$, $Z^1$, $Z^2$ and $X^6$ are the same as defined in <31>, is used as the aromatic compound (B);

<33> The method for production according to <30>, wherein an aromatic compound represented by the formula (6):

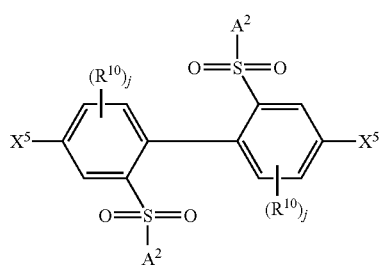

(6)

wherein $A^2$, $R^{10}$, $X^5$ and j are the same as defined in <29>, is used as the aromatic compound (A), and an aromatic compound represented by the formula (6) and structurally different from the aromatic compound (A) or an aromatic compound represented by the formula (7):

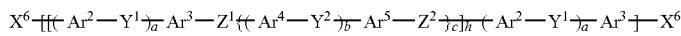

(7)

wherein a, b, c, h, $Ar^2$, $Ar^3$, $Ar^4$, $Ar^5$, $Y^1$, $Y^2$, $Z^1$, $Z^2$ and $X^6$ are the same as defined in <31>, is used as the aromatic compound (B);

<34> The method for production according to any of <22> to <33>, wherein the leaving group is a chlorine atom, a bromine atom, an iodine atom, a trifluoromethylsulfonyloxy group, a C1-C6 alkylsulfonyloxy group or a C6-C10 arylsulfonyloxyl group; and the like.

BEST MODE FOR CARRYING OUT THE PRESENT INVENTION

In the formula of the bipyridine compound (1), $R^1$, $R^2$ and $R^3$ each independently represent a C1-C10 alkyl group which may be substituted, a C1-C5 alkoxy group which may be substituted or a C6-C10 aryl group which may be substituted, and $R^4$, $R^5$, $R^6$, $R^7$ and $R^8$ each independently represent a hydrogen atom or a C1-C3 alkyl group which may be substituted.

Examples of the C1-C10 alkyl group include a linear, branched chain or cyclic alkyl group such as a methyl group, an ethyl group, an n-propyl group, an n-butyl group, an n-hexyl group, an n-nonyl group, an isopropyl group, an isobutyl group, a tert-butyl group, a 2,2-methylpropyl group and a cyclohexyl group, and a C1-C6 alkyl group is preferable and a methyl group, a tert-butyl group and a cyclohexyl group are preferable. The alkyl group may have a substituent or substituents, and examples of the substituent include a phenyl group. Examples of the alkyl group having a substituent or substituents include a benzyl group.

Examples of the C1-C5 alkoxy group include a methoxy group, an ethoxy group, an n-propoxy group, an n-butoxy group, an isopropoxy group, an isobutoxy group, a tert-butoxy group, an n-pentyloxy group and a 2,2-dimethylpropoxy group. The alkoxy group may have a substituent or substituents, and examples of the substituent include a phenyl group. Examples of the alkoxy group having a substituent or substituents include a benzyloxy group.

Examples of the C6-C10 aryl group include a phenyl group, a 4-methylphenyl group, a 3,5-dimethylphenyl group and a 1-naphthyl group, and a phenyl group is preferable. The aryl group may have a substituent or substituents, and examples of the substituent include the above-mentioned C1-C5 alkoxy group, a C2-C10 dialkylamino group such as a dimethylamino group, a C1-C4 perfluoroalkyl group such as a trifluoromethyl group and a C2-C10 acyl group such as an acetyl group. Examples of the aryl group having a substituent or substituents include a 2-dimethylaminophenyl group, a 4-methoxyphenyl group, a 4-trifluoromethylphenyl group and a 4-acetylphenyl group.

Examples of the C1-C3 alkyl group include a methyl group, an ethyl group, an n-propyl group and an isopropyl group.

$R^4$, $R^5$, $R^6$, $R^7$ and $R^8$ are preferably hydrogen atoms;

Examples of the preferable bipyridine compound (1) include the bipyridine compound (1) wherein $R^1$, $R^2$ and $R^3$ each independently is a C1-C10 alkyl group;
the bipyridine compound (1) wherein $R^1$ and $R^2$ each independently is a C1-C10 alkyl group and $R^3$ is a C6-C10 aryl group;
the bipyridine compound (1) wherein $R^1$ is a C1-C10 alkyl group and $R^2$ and $R^3$ each independently is a C6-C10 aryl group;
the bipyridine compound (1) wherein $R^1$, $R^2$ and $R^3$ each independently is a methyl group, an ethyl group, an n-propyl group, an isopropyl group, a tert-butyl group, a cyclohexyl group, a benzyl group, a phenyl group, a 4-methylphenyl group, a methoxy group or an ethoxy group;
the bipyridine compound (1) wherein $R^1$, $R^2$ and $R^3$ are methyl groups;
the bipyridine compound (1) wherein $R^1$ and $R^2$ are methyl groups and $R^3$ is a tert-butyl group;
the bipyridine compound (1) wherein $R^1$ and $R^2$ are methyl groups and $R^3$ is a cyclohexyl group;
the bipyridine compound (1) wherein $R^1$ and $R^2$ are methyl groups and $R^3$ is a phenyl group;
the bipyridine compound (1) wherein $R^1$ is a methyl group and $R^2$ and $R^3$ are phenyl groups;
the bipyridine compound (1) wherein $R^1$, $R^2$ and $R^3$ each independently is a C6-C10 aryl group;
the bipyridine compound (1) wherein $R^1$, $R^2$ and $R^3$ are phenyl groups;
the bipyridine compound (1) wherein $R^1$, $R^2$ and $R^3$ each independently is a C1-C10 alkyl group and $R^4$, $R^5$, $R^6$, $R^7$ and $R^8$ are hydrogen atoms;
the bipyridine compound (1) wherein $R^1$ and $R^2$ each independently is a C1-C10 alkyl group, $R^3$ is a C6-C10 aryl group and $R^4$, $R^5$, $R^6$, $R^7$ and $R^8$ are hydrogen atoms;
the bipyridine compound (1) wherein $R^1$ is a C1-C10 alkyl group, $R^2$ and $R^3$ each independently is a C6-C10 aryl group and $R^4$, $R^5$, $R^6$, $R^7$ and $R^8$ are hydrogen atoms;
the bipyridine compound (1) wherein $R^1$, $R^2$ and $R^3$ each independently is a methyl group, an ethyl group, an n-propyl group, an isopropyl group, a tert-butyl group, a cyclohexyl group, a benzyl group, a phenyl group, a 4-methylphenyl group, a methoxy group or an ethoxy group, and $R^4$, $R^5$, $R^6$, $R^7$ and $R^8$ are hydrogen atoms;
the bipyridine compound (1) wherein $R^1$, $R^2$ and $R^3$ are methyl groups and $R^4$, $R^5$, $R^6$, $R^7$ and $R^8$ are hydrogen atoms;
the bipyridine compound (1) wherein $R^1$ and $R^2$ are methyl groups, $R^3$ is a tert-butyl group and $R^4$, $R^5$, $R^6$, $R^7$ and $R^8$ are hydrogen atoms;
the bipyridine compound (1) wherein $R^1$ and $R^2$ are methyl groups, $R^3$ is a cyclohexyl group and $R^4$, $R^5$, $R^6$, $R^7$ and $R^8$ are hydrogen atoms;
the bipyridine compound (1) wherein $R^1$ and $R^2$ are methyl groups, $R^3$ is a phenyl group and $R^4$, $R^5$, $R^6$, $R^7$ and $R^8$ are hydrogen atoms;
the bipyridine compound (1) wherein $R^1$ is a methyl group, $R^2$ and $R^3$ are phenyl groups and $R^4$, $R^5$, $R^6$, $R^7$ and $R^8$ are hydrogen atoms;
the bipyridine compound (1) wherein $R^1$, $R^2$ and $R^3$ each independently is a C6-C10 aryl group and $R^4$, $R^5$, $R^6$, $R^7$ and $R^8$ are hydrogen atoms; and
the bipyridine compound (1) wherein $R^1$, $R^2$ and $R^3$ are phenyl groups and $R^4$, $R^5$, $R^6$, $R^7$ and $R^8$ are hydrogen atoms.

The bipyridine compound (1) can be produced by reacting a pyridine compound represented by the formula (2):

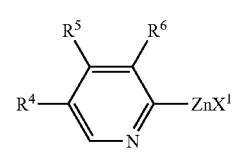

(2)

wherein $R^4$, $R^5$ and $R^6$ are the same as defined above, and $X^1$ represents a halogen atom (hereinafter, simply referred to as the pyridine compound (2)), with a pyridine compound represented by the formula (3):

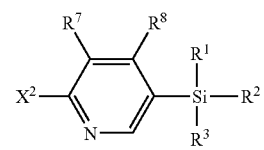

(3)

wherein $R^1$, $R^2$, $R^3$, $R^7$ and $R^8$ are the same as defined above, and $X^2$ represents a halogen atom, a trifluoromethanesulfonyloxy group, a p-toluenesulfonyloxy group or a methanesulfonyloxy group (hereinafter, simply referred to as the pyridine compound (3)), in the presence of a palladium catalyst.

Examples of the halogen atom include a chlorine atom, a bromine atom and an iodine atom.

Examples of the pyridine compound (2) include 2-pyridylzinc chloride, 2-pyridylzinc bromide and 2-pyridylzinc iodide.

The pyridine compound (3) can be produced according to the method described in J. Organomet. Chem., 2000, 612, 117-124. Specifically, the pyridine compound (3) can be produced by reacting a pyridine compound represented by the formula (3') with butyl lithium followed by reacting with the corresponding silane compound as shown in the following Scheme (A):

Scheme (A)

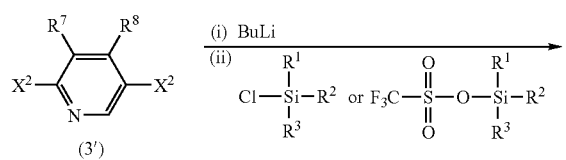

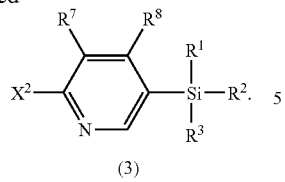

(3)

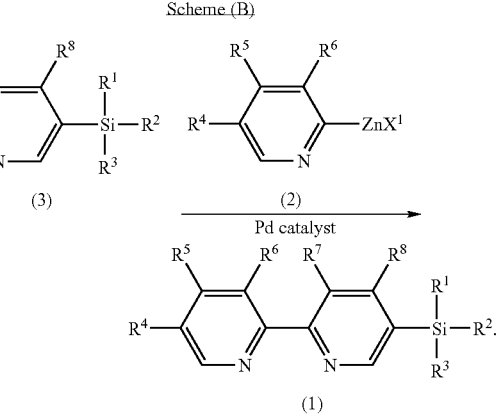

Examples of the pyridine compound represented by the above-mentioned formula (3') include 2,5-dichloropyridine, 2,5-dibromopyridine, 2,5-diiodopyridine, 2-chloro-5-bromopyridine, 2-(5-bromopyridyl)-p-toluenesulfonate and 2-(5-bromopyridyl)-trifluoromethanesulfonate, and 2,5-dibromopyridine is preferable. Examples of the above-mentioned silane compound include trimethylchlorosilane, triethylchlorosilane, tripropylchlorosilane, trihexylchlorosilane, triisopropylchlorosilane, triphenylchlorosilane, tert-butyldimethylchlorosilane, dimethylcyclohexylchlorosilane, benzyldimethylchlorosilane, dimethylphenylchlorosilane, methyldiphenylchlorosilane, 4-methylphenyldimethylchlorosilane, trimethoxychlorosilane, triethoxylchlorosilane, trimethylsilyl trifluoromethanesulfonate, tert-butyldimethylsilyl trifluoromethanesulfonate, dimethylphenylsilyl trifluoromethanesulfonate and methyldiphenylsilyl trifluoromethanesulfonate.

The two reactions shown in Scheme (A) are usually conducted in the presence of an organic solvent. The used amount of the organic solvent is not limited. Examples of the organic solvent include an aromatic hydrocarbon solvent such as benzene, toluene and xylene, and an ether solvent such as 1,4-dioxane, tetrahydrofuran, diethyl ether, tert-butyl methyl ether and ethylene glycol dimethyl ether, and an ether solvent is preferable and tetrahydrofuran, diethyl ether and tert-butyl methyl ether are more preferable.

The reaction temperatures are usually −78 to 120° C., respectively, and the reaction times are usually 1 to 96 hours, respectively.

After completion of the reaction with the silane compound, the pyridine compound (3) can be isolated, for example, by mixing the obtained reaction mixture containing the pyridine compound (3) with water, if necessary, adding a water-insoluble solvent thereto, extracting and then, concentrating the obtained organic layer. The isolated pyridine compound (3) may be further purified by a conventional purification means such as column chromatography, distillation and recrystallization.

Examples of the pyridine compound (3) include 2-bromo-5-trimethylsilylpyridine, 2-bromo-5-(dimethylcyclohexylsilyl)pyridine, 2-bromo-5-(dimethyl-tert-butylsilyl)pyridine, 2-bromo-5-(dimethylphenylsilyl)pyridine, 2-bromo-5-(methyldiphenylsilyl)pyridine and 2-bromo-5-triphenylsilylpyridine.

The reaction of the pyridine compound (2) and the pyridine compound (3) can be carried out according to the method described in J. Org. Chem., 1977, 42, 1821-1823. Specifically, the bipyridine compound (1) can be produced by reacting the pyridine compound (2) with the pyridine compound (3) in the presence of a palladium catalyst as shown in the following Scheme (B):

Examples of the palladium catalyst include tetrakis(triphenylphosphine)palladium, tris(dibenzylideneacetone)dipalladium, tris(dibenzylideneacetone)dipalladium chloroform adduct, bis(1,2-bis(diphenylphosphinoethane))palladium, bis(tricyclohexylphosphine)palladium, bis(tri-tert-butylphosphine)palladium, palladium acetate, palladium trifluoroacetate, palladium chloride, palladium bromide, palladium iodide, palladium cyanide, allylpalladium chloride dimer, crotylpalladium chloride dimmer, 2-methylallylpalladium chloride dimer, palladium acetylacetonate, dichloro(1,5-cyclooctadiene)palladium, dichlorobis(acetonitrile)palladium, dichlorobis(benzonitrile)palladium, dichlorobis(triphenylphosphine)palladium, dichlorobis(tris-o-tolylphosphine)palladium, dichlorobis(tricyclohexylphosphine)palladium and dichloro(1,2-bis(diphenylphosphino)ethane)palladium, and tetrakis(triphenylphosphine)palladium is preferable.

The used amount of the palladium catalyst is usually 0.0005 to 0.5 mole in terms of palladium metal per 1 mole of the pyridine compound (3).

As necessary, a ligand may be used and a phosphine ligand is preferable as the ligand. Specific examples thereof include triphenylphosphine, tris(2-methylphenyl)phosphine, tris(3-methylphenyl)phosphine, tris(4-methylphenyl)phosphine, tris(pentafluorophenyl)phosphine, tris(4-fluorophenyl)phosphine, tris(2-methoxyphenyl)phosphine, tris(3-methoxyphenyl)phosphine, tris(4-methoxyphenyl)phosphine, tris(2,4,6-trimethoxyphenyl)phosphine, tri(3-chlorophenyl)phosphine, tri(4-chlorophenyl)phosphine, tri-n-butylphosphine, tri-tert-butylphosphine, tricyclohexylphosphine, 1,2-diphenylphosphinoethane, 1,3-diphenylphosphinopropane, 1,4-diphenylphosphinobutane, 1,2-dicyclohexylphosphinoethane, 1,3-dicyclohexylphosphinopropane, 1,4-dicyclohexylphosphinobutane, 1,2-dimethylphosphinoethane, 1,3-dimethylphosphinopropane, 1,4-dimethylphosphinobutane, 1,2-diethylphosphinoethane, 1,3-diethylphosphinopropane, 1,4-diethylphosphinobutane, 1,2-diisopropylphosphinoethane, 1,3-diisopropylphosphinopropane, 1,4-diisopropylphosphinobutane, tri-2-furylphosphine, 2-(dicyclohexylphosphino)biphenyl, 2-(di-tert-butylphosphino)biphenyl, 2-di-tert-butylphosphino-2'-methylbiphenyl, 2-(dicyclohexylphosphino-2',6'-dimethoxy-1,1'-biphenyl, 2-(dicyclohexylphosphino)-2'-(N,N-dimethylamino)biphenyl, 2-dicyclohexylphosphino-2'-methyl-biphenyl, 2-(dicyclohexylphosphino)-2',4',6'-tri-isopropyl-1,1'-biphen yl, 1,1'-bis(diphenylphosphino)ferrocene and 1,1'-bis(di-isopropylphosphino)ferrocene.

The used amount of the ligand is usually 1 to 10 moles and preferably 1 to 5 moles per 1 mole of the palladium catalyst.

The reaction of the pyridine compound (2) and the pyridine compound (3) is usually conducted in the presence of a solvent and the used amount thereof is not limited. Examples of the solvent include an aromatic hydrocarbon solvent such as benzene, toluene and xylene, and an ether solvent such as 1,4-dioxane, tetrahydrofuran, diethyl ether, tert-butyl methyl ether and ethylene glycol dimethyl ether, and an ether solvent is preferable and tetrahydrofuran, diethyl ether and tert-butyl methyl ether are more preferable.

The reaction temperature is usually 0 to 150° C., and the reaction time is usually 20 minutes to 96 hours.

After completion of the reaction, the bipyridine compound (1) can be isolated, for example, by mixing the reaction mixture with ammonia water, if necessary, adding a water-insoluble solvent thereto, extracting and then, concentrating the obtained organic layer. The isolated bipyridine compound (1) may be further purified by a conventional purification means such as column chromatography, distillation and recrystallization.

A transition metal complex can be produced by contacting the bipyridine compound (1) with a compound of a transition metal belonging to Group 9, 10 or 11.

Examples of the compound of a transition metal belonging to Group 9, 10 or 11 include a cobalt compound, a nickel compound, a copper compound, a rhodium compound, a palladium compound, an iridium compound and a platinum compound. Among them, a compound of a transition metal belonging to Group 10 is preferable and a nickel compound is more preferable.

Examples of the nickel compound include bis(1,5-cyclooctadiene)nickel(0); a nickel halide such as nickel fluoride, nickel chloride, nickel bromide and nickel iodide; a nickel carboxylate such as nickel formate, nickel acetate, nickel 2-ethylhexanoate, nickel cyclobutanoate, nickel oxalate, nickel stearate, nickel naphthenate and nickel citrate; nickel hypophosphite; nickel sulfate; nickel carbonate; nickel nitrate; and nickel acetylacetonate. Among the nickel compounds, a nickel compound having a coordinating ether compound such as 1,2-dimethoxyethane and 2-methoxyethyl ether and a hydrate exist, and the nickel compound having a coordinating ether compound and the hydrate may be used.

Among them, bis(1,5-cyclooctadiene)nickel(0), nickel fluoride (II), nickel chloride (II), nickel bromide (II), nickel iodide (II), nickel acetate (II) and nickel nitrate (II) are preferable.

The contact of the compound of a transition metal belonging to Group 9, 10 or 11 and the bipyridine compound (1) is usually carried out by mixing the both in a solvent. Examples of the solvent include water, an organic solvent and a mixed solvent of water and an organic solvent. Examples of the organic solvent include an aromatic hydrocarbon solvent such as benzene, toluene and xylene; an ether solvent such as 1,4-dioxane, tetrahydrofuran, diethyl ether, tert-butyl methyl ether and ethylene glycol dimethyl ether; an alcohol solvent such as methanol, ethanol and isopropanol; an amide solvent such as N,N-dimethyl formamide, N,N-dimethylacetamide and N-methyl-2-pyrrolidone; and a sulfoxide solvent such as dimethylsulfoxide.

The contact temperature is usually −78 to 200° C.

The compound of a transition metal belonging to Group 9, or 11 may be contacted with the bipyridine compound (1) in the presence of a suitable additive (for example, reducing agent etc.).

The transition metal complex can be isolated by concentrating a mixture obtained by contacting the compound of a transition metal belonging to Group 9, 10 or 11 with the bipyridine compound (1). The isolated transition metal complex may be further purified by a conventional purification means such as recrystallization. Additionally, the obtained mixture containing the transition metal complex may be used as it is for the following method of production of a conjugated aromatic compound.

Examples of thus obtained transition metal complex include the transition metal complex obtained by contacting the bipyridine compound (1) wherein $R^1$, $R^2$ and $R^3$ each independently is a C1-C10 alkyl group with the nickel compound;

the transition metal complex obtained by contacting the bipyridine compound (1) wherein $R^1$ and $R^2$ each independently is a C1-C10 alkyl group and $R^3$ is a C6-C10 aryl group with the nickel compound;

the transition metal complex obtained by contacting the bipyridine compound (1) wherein $R^1$ is a C1-C10 alkyl group and $R^2$ and $R^3$ each independently is a C6-C10 aryl group with the nickel compound;

the transition metal complex obtained by contacting the bipyridine compound (1) wherein $R^1$, $R^2$ and $R^3$ each independently is a methyl group, an ethyl group, an n-propyl group, an isopropyl group, a tert-butyl group, a cyclohexyl group, a benzyl group, a phenyl group, a 4-methylphenyl group, a methoxy group or an ethoxy group with the nickel compound;

the transition metal complex obtained by contacting the bipyridine compound (1) wherein $R^1$, $R^2$ and $R^3$ are methyl groups with the nickel compound;

the transition metal complex obtained by contacting the bipyridine compound (1) wherein $R^1$ and $R^2$ are methyl groups and $R^3$ is a tert-butyl group with the nickel compound;

the transition metal complex obtained by contacting the bipyridine compound (1) wherein $R^1$ and $R^2$ are methyl groups and $R^3$ is a cyclohexyl group with the nickel compound;

the transition metal complex obtained by contacting the bipyridine compound (1) wherein $R^1$ and $R^2$ are methyl groups and $R^3$ is a phenyl group with the nickel compound;

the transition metal complex obtained by contacting the bipyridine compound (1) wherein $R^1$ is a methyl group and $R^2$ and $R^3$ are phenyl groups with the nickel compound;

the transition metal complex obtained by contacting the bipyridine compound (1) wherein $R^1$, $R^2$ and $R^3$ each independently is a C6-C10 aryl group with the nickel compound;

the transition metal complex obtained by contacting the bipyridine compound (1) wherein $R^1$, $R^2$ and $R^3$ are phenyl groups with the nickel compound;

the transition metal complex obtained by contacting the bipyridine compound (1) wherein $R^1$, $R^2$ and $R^3$ each independently is a C1-C10 alkyl group and $R^4$, $R^5$, $R^6$, $R^7$ and $R^8$ are hydrogen atoms with the nickel compound;

the transition metal complex obtained by contacting the bipyridine compound (1) wherein $R^1$ and $R^2$ each independently is a C1-C10 alkyl group, $R^3$ is a C6-C10 aryl group and $R^4$, $R^5$, $R^6$, $R^7$ and $R^8$ are hydrogen atoms with the nickel compound;

the transition metal complex obtained by contacting the bipyridine compound (1) wherein $R^1$ is a C1-C10 alkyl group, $R^2$ and $R^3$ each independently is a C6-C10 aryl group and $R^4$, $R^5$, $R^6$, $R^7$ and $R^8$ are hydrogen atoms with the nickel compound;

the transition metal complex obtained by contacting the bipyridine compound (1) wherein $R^1$, $R^2$ and $R^3$ each independently is a methyl group, an ethyl group, an n-propyl group, an isopropyl group, a tert-butyl group, a cyclohexyl group, a benzyl group, a phenyl group, a 4-methylphenyl group, a methoxy group or an ethoxy group, and $R^4$, $R^5$, $R^6$, $R^7$ and $R^8$ are hydrogen atoms with the nickel compound;

the transition metal complex obtained by contacting the bipyridine compound (1) wherein $R^1$, $R^2$ and $R^3$ are methyl groups and $R^4$, $R^5$, $R^6$, $R^7$ and $R^8$ are hydrogen atoms with the nickel compound;

the transition metal complex obtained by contacting the bipyridine compound (1) wherein $R^1$ and $R^2$ are methyl groups, $R^3$ is a tert-butyl group and $R^4$, $R^5$, $R^6$, $R^7$ and $R^8$ are hydrogen atoms with the nickel compound;

the transition metal complex obtained by contacting the bipyridine compound (1) wherein $R^1$ and $R^2$ are methyl groups, $R^3$ is a cyclohexyl group and $R^4$, $R^5$, $R^6$, $R^7$ and $R^8$ are hydrogen atoms with the nickel compound;

the transition metal complex obtained by contacting the bipyridine compound (1) wherein $R^1$ and $R^2$ are methyl groups, $R^3$ is a phenyl group and $R^4$, $R^5$, $R^6$, $R^7$ and $R^8$ are hydrogen atoms with the nickel compound;

the transition metal complex obtained by contacting the bipyridine compound (1) wherein $R^1$ is a methyl group, $R^2$ and $R^3$ are phenyl groups and $R^4$, $R^5$, $R^6$, $R^7$ and $R^8$ are hydrogen atoms with the nickel compound;

the transition metal complex obtained by contacting the bipyridine compound (1) wherein $R^1$, $R^2$ and $R^3$ each independently is a C6-C10 aryl group and $R^4$, $R^5$, $R^6$, $R^7$ and $R^8$ are hydrogen atoms with the nickel compound; and the transition metal complex obtained by contacting the bipyridine compound (1) wherein $R^1$, $R^2$ and $R^3$ are phenyl groups and $R^4$, $R^5$, $R^6$, $R^7$ and $R^8$ are hydrogen atoms with the nickel compound.

Next, a method for production of a conjugated aromatic compound comprising reacting an aromatic compound (A) wherein one or two leaving groups are bonded to an aromatic ring with an aromatic compound (A) having the same structure as that of the above-mentioned aromatic compound (A) or an aromatic compound (B) being structurally different from the above-mentioned aromatic compound (A) and having one or two leaving groups bonded to an aromatic ring, in the presence of the transition metal complex will be illustrated.

The aromatic compound (A) and the aromatic compound (B) compounds having at least one aromatic ring and one or two leaving groups bonded to an aromatic ring.

The aromatic compound (B) is structurally different from the aromatic compound (A).

Examples of the aromatic ring include an aromatic hydrocarbon ring such as a benzene ring, a biphenyl ring, a naphthalene ring, a fluorene ring, an anthracene ring and a phenanthrene ring, and a heteroaromatic ring such as a thiophene ring, a pyrrole ring, a pyridine ring, a pyrimidine ring, a quinoline ring, an isoquinoline ring and a quinoxaline ring.

The aromatic ring may be substituted with at least one group uninvolved in the reaction, and specific examples of the group uninvolved in the reaction include the following (a1) to (g1).

(a1) a C1-C20 alkyl group which may be substituted with at least one substituent selected from the group consisting of a fluorine atom, a cyano group, a C1-C20 alkoxy group, a C6-C20 aryl group and a C6-C20 aryloxy group;

(b1) a C1-C20 alkoxy group which may be substituted with at least one substituent selected from the group consisting of a fluorine atom, a cyano group, a C1-C20 alkoxy group, a C6-C20 aryl group and a C6-C20 aryloxy group;

(c1) a C6-C20 aryl group which may be substituted with at least one substituent selected from the group consisting of a fluorine atom, a cyano group, a C1-C20 alkoxy group and a C6-C10 aryloxy group;

(d1) a C6-C20 aryloxy group which may be substituted with at least one substituent selected from the group consisting of a fluorine atom, a cyano group, a C1-C20 alkoxy group and a C6-C20 aryloxy group;

(e1) a C2-C20 acyl group which may be substituted with at least one substituent selected from the group consisting of a fluorine atom, a cyano group, a C1-C20 alkoxy group, a C6-C20 aryl group and a C6-C20 aryloxy group;

(f1) a C2-C20 acyloxy group which may be substituted with at least one substituent selected from the group consisting of a fluorine atom, a cyano group, a C1-C20 alkoxy group, a C6-C20 aryl group and a C6-C20 aryloxy group;

(g1) a C6-C20 arylsulfonyl group which may be substituted with at least one substituent selected from the group consisting of a fluorine atom, a cyano group, a C1-C20 alkoxy group, a C6-C20 aryl group and a C6-C20 aryloxy group; and (h1) a group represented by the following formula:

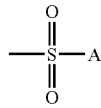

wherein A represents an amino group substituted with one or two C1-C20 hydrocarbon groups or a C1-C20 alkoxy group, and the above-mentioned hydrocarbon group and the above-mentioned alkoxy group may be substituted with at least one group selected from the group consisting of a fluorine atom, a C1-C20 alkoxy group, a C6-C20 aryl group, a C6-C20 aryloxy group, a C2-C20 acyl group and a cyano group;

(i1) a cyano group; and (j1) a fluorine atom.

Examples of the C1-C20 alkoxy group in the above-mentioned (a1) to (h1) include a methoxy group, an ethoxy group, an n-propoxy group, an isopropoxy group, an n-butoxy group, a sec-butoxy group, a tert-butoxy group, an n-pentyloxy group, a 2,2-dimethylpropoxy group, an n-hexyloxy group, a cyclohexyloxy group, an n-heptyloxy group, an n-octyloxy group, an n-nonyloxy group, an n-decyloxy group, an n-undecyloxy group, an n-dodecyloxy group, an n-tridecyloxy group, an n-tetradecyloxy group, an n-pentadecyloxy group, an n-hexadecyloxy group, an n-heptadecyloxy group, an n-octadecyloxy group, an n-nonadecyloxy group and an n-icosyloxy group, and a C1-C6 alkoxy group is preferable.

Examples of the C6-C20 aryl group in the above-mentioned (a1) to (h1) include a phenyl group, a 4-methylphenyl group, a 2-methylphenyl group, a 1-naphthyl group, a 2-naphthyl group, a 3-phenanthryl group and a 2-anthryl group.

Examples of the C6-C20 aryloxy group in the above-mentioned (a1) to (h1) include those composed of the above-mentioned C6-C20 aryl group and an oxygen atom such as a phenoxy group, a 4-methylphenoxy group, a 2-methylphenoxy group, a 1-naphthyloxy group, a 2-naphthyloxy group, a 3-phenanthryloxy group and a 2-anthryloxy group.

Examples of the C1-C20 alkyl group in the above-mentioned (a1) include a methyl group, an ethyl group, an n-propyl group, an isopropyl group, an n-butyl group, an isobutyl group, a sec-butyl group, a tert-butyl group, an n-pentyl group, a 2,2-methylpropyl group, a cyclopentyl group, an n-hexyl group, a cyclohexyl group, an n-heptyl group, a 2-methylpentyl group, an n-octyl group, a 2-ethylhexyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group and an n-icosyl group.

Examples of the C2-C20 acyl group in the above-mentioned (e1) and (h1) include a C2-C20 aliphatic or aromatic acyl group such as an acetyl group, a propionyl group, a butyryl group, an isobutyryl group, a benzoyl group, a 1-naphthoyl group and a 2-naphthoyl group.

Examples of the C2-C20 acyloxy group in the above-mentioned (f1) include those composed of the above-mentioned C2-C20 acyl group and an oxygen atom such as an acetyloxy group, a propionyloxy group, a butyryloxy group, an isobutyryloxy group, a benzoyloxy group, a 1-naphthoyloxy group and a 2-naphthoyloxy group.

Examples of the C6-C20 aryl sulfonyl group in the above-mentioned (g1) include a phenylsulfonyl group and a p-toluenesulfonyl group.

Examples of the hydrocarbon group in the above-mentioned (h1) include a methyl group, an ethyl group, an n-propyl group, an isopropyl group, an n-butyl group, an isobutyl group, a sec-butyl group, a tert-butyl group, an n-pentyl group, a 2,2-methylpropyl group, an n-hexyl group, a cyclohexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-icosyl group, a phenyl group, a 1,3-butadiene-1,4-diyl group, a butane-1,4-diyl group, a pentane-1,5-diyl group, a biphenyl-2,2'-diyl group and an o-xylylene group. Examples of the amino group substituted with one or two hydrocarbon groups wherein sum of carbon atoms of the hydrocarbon groups is 3 to 20 include a diethylamino group, an n-propylamino group, a di-n-propylamino group, an isopropylamino group, a diisopropylamino group, an n-butylamino group, a di-n-butylamino group, a sec-butylamino group, a di-sec-butylamino group, a tert-butylamino group, a di-tert-butylamino group, an n-pentylamino group, a 2,2-dimethylpropylamino group, an n-hexylamino group, a cyclohexylamino group, an n-heptylamino group, an n-octylamino group, an n-nonylamino group, an n-decylamino group, an n-undecylamino group, an n-dodecylamino group, an n-tridecylamino group, an n-tetradecylamino group, an n-pentadecylamino group, an n-hexadecylamino group, an n-heptadecylamino group, an n-octadecylamino group, an n-nonadecylamino group, an n-icosylamino group, a pyrrolyl group, a pyrrolidinyl group, a piperidinyl group, a carbazolyl group, a dihydroindolyl group and a dihydroisoindolyl group.

As (a1), a C1-C20 unsubstituted alkyl group, a C1-C20 alkyl group substituted with one or two or more fluorine atoms such as a trifluoromethyl group, a C1-C20 alkyl group substituted with a C1-C20 alkoxy group such as a methoxymethyl group and a C1-C20 alkyl group substituted with a cyano group such as a cyanomethyl group are preferable.

As (b1), a C1-C20 unsubstituted alkoxy group and a C1-C20 alkoxy group substituted with a C1-C20 alkoxy group such as a methoxymethoxy group are preferable.

As (c1), a C6-C20 unsubstituted aryl group is preferable.

As (d1), a C6-C20 unsubstituted aryloxy group is preferable.

As (e1), a C2-C20 unsubstituted acyl group and a C2-C20 acyl group substituted with a C6-C20 aryloxy group such as a phenoxybenzoyl group are preferable.

As (f1), a C2-C20 unsubstituted acyloxy group and a C2-C20 acyloxy group substituted with a C6-C20 aryloxy group such as a phenoxybenzoyloxy group are preferable.

As (g1), a C6-C20 unsubstituted arylsulfonyl group is preferable.

As (h1), A is preferably an isopropoxy group, a 2,2-dimethypropoxy group, a cyclohexyloxy group, a diethylamino group or an n-dodecylamino group and A is more preferably an isopropoxy group, a 2,2-dimethylpropoxy group or a cyclohexyloxy group.

As the group uninvolved in the reaction, the above-mentioned (a1), (b1), (e1) and (h1) are preferable.

Examples of the leaving group include a chlorine atom, a bromine atom, an iodine atom, a C1-C6 alkylsulfonyloxy group such as a trifluoromethylsulfonyloxy group, a methanesulfonyloxy group and an ethylsulfonyloxy group, and a C6-C10 arylsulfonyloxy group such as a phenylsulfonyloxy group and a p-methylphenylsulfonyloxy group, and a chlorine atom, a bromine atom and an iodine atom are preferable and a chlorine atom and a bromine atom are more preferable.

Specific examples of the aromatic compound include an aromatic compound represented by the formula (4):

(hereinafter, simply referred to as the aromatic compound (4)).

In the formula (4), $Ar^1$ represents an n-valent aromatic group, and the aromatic ring composed of the above-mentioned aromatic group is a benzene ring, a biphenyl ring, a naphthalene ring, a fluorene ring, an anthracene ring, a phenanthrene ring, a thiophene ring, a pyrrole ring, a pyridine ring, a pyrimidine ring, a quinoline ring, an isoquinoline ring or a quinoxaline ring, and is an aromatic ring which may be substituted with at least one group uninvolved in the reaction. Additionally, $X^3$ represents a leaving group, n represents 1 or 2. When n is 2, $X^3$s may be same or different each other.

Examples of the group uninvolved in the reaction include the same as described above.

Examples of the leaving group include the same as described above, and a chlorine atom, a bromine atom and an iodine atom are preferable and a chlorine atom and a bromine atom are more preferable.

Examples of the aromatic compound (4) include chlorobenzene, bromobenzene, iodobenzene, 4-chlorofluorobenzene, 3-chlorofluorobenzene, 2-chlorofluorobenzene, 4-chlorobenzonitrile, 3-chlorobenzonitrile, 2-chlorotoluene, 2,5-dimethylchlorobenzene, 2-ethylchlorobenzene, 3-n-propylchlorobenzene, 4-isopropylchlorobenzene, 5-n-butylchlorobenzene, 2-isobutylchlorobenzene, 3-sec-butylchlorobenzene, 4-tert-butylchlorobenzene, 5-(2,2-dimethylpropyl)chlorobenzene, 2-n-hexylchlorobenzene, 4-cyclohexylchlorobenzene, 4-chlorobiphenyl, 2-chlorobiphenyl, 4-benzylchlorobenzene, 4-chlorobenzotrifluoride, 2-chlorobenzotrifluoride, 4-chlorobenzotrichloride, 3-chlorobenzotrichloride, 2-chlorobenzotrichloride, (4-chlorophenyl)acetonitrile, 4-chloroanisole, 2,3-dimethoxychlorobenzene, 2,4-dimethoxychlorobenzene, 2,5-dimethoxychlorobenzene, 2-ethoxychlorobenzene, 3-n-propoxychlorobenzene, 4-isopropoxychlorobenzene, 5-n-butoxychlorobenzene, 4-tert-butoxychlorobenzene, 4-phenoxychlorobenzene, 4-benzyloxychlorobenzene, 4-(methoxymethyl)chlorobenzene, 4-(n-butoxymethyl)chlorobenzene, 4-(methoxymethyl)chlorobenzene, 4-(benzyloxymethoxy)chlorobenzene, 4-{2-(n-butoxy)ethoxy}chlorobenzene, 3-chloroacetophenone, 2-chloroacetophenone, 4-chloropropiophenone, 1-(4-chlorophenyl)-2,2-dimethylpropanone, (4-chlorophenyl)cyclohexane, 4-chlorobenzophenone, 4-chlorobenzalacetophenone, 1-(4-chlorophenyl)-3-phenyl-2-propen-1-one, 3-(4-chlorophenyl)-1-phenyl-2-propen-1-one, methyl 4-chlorobenzoate, methyl 2-chlorobenzoate, ethyl 3-chlorobenzoate, n-propyl 4-chlorobenzoate, n-butyl 3-chlorobenzoate, 2,2-dimethylpropyl 2-chlorobenzoate, phenyl 4-chlorobenzoate, methyl p-chlorophenylacetate, methyl 3-(4-chlorophenyl)propionate, methyl p-chlorocinnamate, 4-chlorophenyl acetate, 2-chlorophenyl acetate, 4-chlorophenyl propionate, 4-chlorophenyl pivalate, 4-(tert-butoxycarbonyloxy)chlorobenzene, 4-chlorobenzyl acetate, (4-chlorophenyl)methyl sulfoxide, (4-chlorophenyl)phenyl sulfoxide, (4-chlorophenyl)ethyl sulfone, methyl 4-chlorobenzenesulfonate, methyl 3-chlorobenzenesulfonate, methyl 2-chlorobenzenesulfonate, ethyl 4-chlorobenzenesulfonate, 2,2-dimethylpropyl 4-chlorobenzenesulfonate, 2,2-dimethylpropyl 3-chlorobenzenesulfonate, 2,2-dimethylpropyl 2-chlorobenzenesulfonate, phenyl 4-chlorobenzenesulfonate, phenyl 3-chlorobenzenesulfonate, phenyl 2-chlorobenzenesulfonate, 4-chlorophenyl methanesulfonate, 2-chlorophenyl methanesulfonate, 4-chlorophenyl benzenesulfonate, 3-chlorophenyl p-toluenesulfonate, 2-(4-chlorophenyl)pyridine, 3-(4-chlorophenyl)pyridine, 4-(4-chlorophenyl)pyridine, 1-(4-chlorophenyl)pyrrole, 2-(4-chlorophenyl)pyrrole, 3-(4-chlorophenyl)pyrrole, N,N-dimethyl-4-chlorobenzylamine, N-(4-chlorophenyl)acetamide, N-(4-chlorophenyl)-N-methylacetamide, N-(4-chlorophenyl)-N-phenylacetamide, (4-chlorophenyl)benzoic acid amide, tert-butyl N-(4-chlorophenyl)carbamate, N-(4-chlorobenzyl)acetamide, 4-chlorobenzenesulfonamide, 4-chlorobenzenesulfonic acid dimethylamide, methanesulfonic acid 4-chloroanilide, p-toluenesulfonic acid 4-benzylamide, 1-chloro-4-(trimethylsilyl)benzene, 1-chloro-4-(tert-butyldimethylsilyl)benzene, 1-chloro-4-(trimethylsilyloxy)benzene, 1-chloro-4-(triethylsilyloxy)benzene, 1-chloro-4-(triisopropylsilyloxy)benzene, 1-chloro-4-(triphenylsilyloxy)benzene, 1-chloro-4-(phenyldimethylsilyloxy)benzene, 4-chloroindane, 4-chloroindene, 1-chloronaphthalene, 2-bromothiophene, 5-bromo-3-hexylthiophene, 2-bromo-3-dodecylthiophene, 5-bromo-2,2'-bithiophene, 5-bromo-3-cyclohexylthiophene, 2-chloro3-octylthiophene, 5-chloro-3-phenylthiophene, 1-methyl-5-chloropyrrole, 1-hexyl-2-bromopyrrole, 1-octyl-5-chloropyrrole, 2-chloropyridine, 3-chloropyridine, 5-bromopyridine, 3-methyl-2-chloropyridine, 3-hexyl-5-chloropyridine, 5-chloro-2,2'-bipyridine, 3,3'-dimethyl-5-chloro-2,2'-bipyridine, 3,3'-dioctyl-5-bromo-2,2'-bipyridine, 2-chloropyrimidine, 5-chloropyrimidine, 2-bromopyrimidine, 5-chloroquinoline, 8-bromoquinoline, 2-chloroquinoline, 1-chloroisoquinoline, 4-chloroisoquinoline, 8-bromoisoquinoline, 5-bromoisoquinoline, 4-bromo-2,1,3-benzothiazole, 7-chlorobenzimidazole, 4-chlorobenzimidazole, 5-chloroquinoxaline, 5-chloro-2,3-diphenylquinoxaline, 2-bromoquinoxaline, 6-bromoquinoxaline, 1,3-dichlorobenzene, 1,4-dibromobenzene, 1,4-diiodobenzene, 2,4-dichlorotoluene, 3,5-dibromotoluene, 2,5-diiodotoluene, 1,3-dichloro-4-methoxybenzene, 1,4-dibromo-3-methoxybenzene, 1,4-diiodo-3-methoxybenzene, 1,3-dichloro-4-acetoxybenzene, 1,4-dibromo-3-acetoxybenzene, 1,3-diiodo-4-acetoxybenzene, 2,5-dichloro-4'-phenoxybenzophenone, 1,4-dibromo-2-ethylbenzene, 1,4-dibromo-2-methoxybenzene, dimethyl 2,5-dibromoterephthalate, 1,4-dibromonaphthalene, 1,1'-dibromo-4,4'-biphenyl, 1,4-dibromo-2,5-dihexyloxybenzene, 1-bromo-4-chlorobenzene, 1-bromo-4-chlorotoluene, 1-bromo-4-chloro-2-propylbenzene, 2,5-dibromo-4'-phenoxybenzophenone, 2,5-dibromothiophene, 2,5-dibromo-3-hexylthiophene, 2,5-dibromo-3-dodecylthiophene, 5,5'-dibromo-2,2'-bithiophene, 2,5-dibromo-3-cyclohexylthiophene, 2,5-dichloro-3-octylthiophene, 2,5-dichloro-3-phenylthiophene, 1-methyl-2,5-dichloropyrrole, 1-hexyl-2,5-dibromopyrrole, 1-octyl-2,5-dichloropyrrole, 2,5-dichloropyridine, 3,5-dichloropyridine, 2,5-dibromopyridine, 3-methyl-2,5-dichloropyridine, 3-hexyl-2,5-dichloropyridine, 5,5'-dichloro-2,2'-bipyridine, 3,3'-dimethyl-5,5'-dichloro-2,2'-bipyridine, 3,3'-dioctyl-5,5'-dibromo-2,2'-bipyridine, 2,5-dichloropyrimidine, 2,5-dibromopyrimidine, 5,8-dichloroquinoline, 5,8-dibromoquinoline, 2,6-dichloroquinoline, 1,4-dichloroisoquinoline, 5,8-dichloroisoquinoline, 4,7-dibromo-2,1,3-benzothiadizole, 4,7-dichlorobenzimidazole, 5,8-dichloroquinoxaline, 5,8-dichloro-2,3-diphenylquinoxaline, 2,6-dibromoquinoxaline, 2,7-dibromo-9,9-dihexyl-9H-fluorene, 2,7-dibromo-9,9-dioctyl-9H-fluorene, 2,7-dibromo-9,9-didodecyl-9H-fluorene, 2,7-dichloro-9,9-dihexyl-9H-fluorene, 2,7-dichloro-9,9-dioctyl-9H-fluorene, 2,7-dichloro-9,9-didodecyl-9H-fluorene, 2-bromo-7-chloro-9,9-dihexyl-9H-fluorene, 2-bromo-7-chloro-9,9-dioctyl-9H-fluorene and 2-bromo-7-chloro-9,9-didodecyl-9H-fluorene.

Specific examples of the aromatic compound also include an aromatic compound represented by the formula (5):

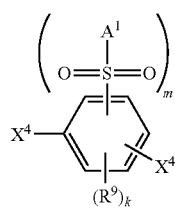

(5)

(hereinafter, simply referred to as the aromatic compound (5)).

In the formula (5), as $A^1$, a C3-C20 unsubstituted alkoxy group is preferable and an isopropyl group, an isobutoxy group, a 2,2-dimethylpropoxy group and a cyclohexyloxy group are more preferable.

Examples of the C1-C20 alkyl group, the C1-C20 alkoxy group, the C6-C20 aryl group, the C6-C20 aryloxy group and the C2-C20 acyl group in $R^9$ include the same as described above, respectively. As $R^9$, a hydrogen atom, a C1-C20 unsubstituted alkyl group and a C1-C20 unsubstituted alkoxy group are preferable and a hydrogen atom is more preferable.

As $X^4$, a chlorine atom and a bromine atom are preferable and m is preferably 1.

Examples of the aromatic compound (5) include isopropyl 2,5-dichlorobenzenesulfonate, isobutyl 2,5-dichlorobenzenesulfonate, 2,2-dimethylpropyl 2,5-dichlorobenzenesulfonate, cyclohexyl 2,5-dichlorobenzenesulfonate, n-octyl 2,5-dichlorobenzenesulfonate, n-pentadecyl 2,5-dichlorobenzenesulfonate, n-icosyl 2,5-dichlorobenzenesulfonate, N,N-diethyl-2,5-dichlorobenzenesulfonamide, N,N-diisopropyl-2,5-dichlorobenzenesulfonamide, N-(2,2-dimethylpropyl)-2,5-dichlorobenzenesulfonamide, N-n-dodecyl-2,5-dichlorobenzenesulfonamide, N-n-icosyl-2,5-dichlorobenzenesulfonamide, isopropyl 3,5-dichlorobenzenesulfonate, isobutyl 3,5-dichlorobenzenesulfonate, 2,2-dimethylpropyl 3,5-dichlorobenzenesulfonate, cyclohexyl 3,5-dichlorobenzenesulfonate, n-octyl 3,5-dichlorobenzenesulfonate, n-pentadecyl 3,5-dichlorobenzenesulfonate, n-icosyl 3,5-dichlorobenzenesulfonate, N,N-diethyl-3,5-dichlorobenzenesulfonamide, N,N-diisopropyl-3,5-dichlorobenzenesulfonamide, N-(2,2-dimethylpropyl)-3,5- dichlorobenzenesulfonamide, N-n-dodecyl-3,5-dichlorobenzenesulfonamide, N-n-icosyl-3,5-dichlorobenzenesulfonamide, isopropyl 2,5-dibromobenzenesulfonate, isobutyl 2,5-dibromobenzenesulfonate, 2,2-dimethylpropyl 2,5-dibromobenzenesulfonate, cyclohexyl 2,5-dibromobenzenesulfonate, n-octyl 2,5-dibromobenzenesulfonate, n-pentadecyl 2,5-dibromobenzenesulfonate, n-icosyl 2,5-dibromobenzenesulfonate, N,N-diethyl-2,5-dibromobenzenesulfonamide, N,N-diisopropyl-2,5-dibromobenzenesulfonamide, N-(2,2-dimethylpropyl)-2,5-dibromobenzenesulfonamide, N-n-dodecyl-2,5-dibromobenzenesulfonamide, N-n-icosyl-2,5-dibromobenzenesulfonamide, isopropyl 3,5-dibromobenzenesulfonate, isobutyl 3,5-dibromobenzenesulfonate, 2,2-dimethylpropyl 3,5-dibromobenzenesulfonate, cyclohexyl 3,5-dibromobenzenesulfonate, n-octyl 3,5-dibromobenzenesulfonate, n-pentadecyl 3,5-dibromobenzenesulfonate, n-icosyl 3,5-dibromobenzenesulfonate, N,N-diethyl-3,5-dibromobenzenesulfonamide, N,N-diisopropyl-3,5-dibromobenzenesulfonamide, N-(2,2-dimethylpropyl)-3,5-dibromobenzenesulfonamide, N-n-dodecyl-3,5-dibromobenzenesulfonamide, N-n-icosyl-3,5-dibromobenzenesulfonamide, isopropyl 2,5-diiodobenzenesulfonate, isobutyl 2,5-diiodobenzenesulfonate, 2,2-dimethylpropyl 2,5-diiodobenzenesulfonate, cyclohexyl 2,5-diiodobenzenesulfonate, n-octyl 2,5-diiodobenzenesulfonate, n-pentadecyl 2,5-diiodobenzenesulfonate, n-icosyl 2,5-diiodobenzenesulfonate, N,N-diethyl-2,5-diiodobenzenesulfonamide, N,N-diisopropyl-2,5-diiodobenzenesulfonamide, N-(2,2-dimethylpropyl)-2,5-diiodobenzenesulfonamide, N-n-dodecyl-2,5-diiodobenzenesulfonamide, N-n-icosyl-2,5-diiodobenzenesulfonamide, isopropyl 3,5-diiodobenzenesulfonate, isobutyl 3,5-diiodobenzenesulfonate, 2,2-dimethylpropyl 3,5-diiodobenzenesulfonate, cyclohexyl 3,5-diiodobenzenesulfonate, n-octyl 3,5-diiodobenzenesulfonate, n-pentadecyl 3,5-diiodobenzenesulfonate, n-icosyl 3,5-diiodobenzenesulfonate, N,N-diethyl-3,5-diiodobenzenesulfonamide, N,N-diisopropyl-3,5-diiodobenzenesulfonamide, N-(2,2-dimethylpropyl)-3,5-diiodobenzenesulfonamide, N-n-dodecyl-3,5-diiodobenzenesulfonamide, N-n-icosyl-3,5-diiodobenzenesulfonamide, 2,2-dimethylpropyl 2,4-dichlorobenzenesulfonate, 2,2-dimethylpropyl 2,4-dibromobenzenesulfonate, 2,2-dimethylpropyl 2,4-diiodobenzenesulfonate, 2,2-dimethylpropyl 2,4-dichloro-5-methylbenzenesulfonate, 2,2-dimethylpropyl 2,5-dichloro-4-methylbenzenesulfonate, 2,2-dimethylpropyl 2,4-dibromo-5-methylbenzenesulfonate, 2,2-dimethylpropyl 2,5-dibromo-4-methylbenzenesulfonate, 2,2-dimethylpropyl 2,4-diiodo-5-methylbenzenesulfonate, 2,2-dimethylpropyl 2,5-diiodo-4-methylbenzenesulfonate, 2,2-dimethylpropyl 2,4-dichloro-5-methoxybenzenesulfonate, 2,2-dimethylpropyl 2,5-dichloro-4-methoxybenzenesulfonate, 2,2-dimethylpropyl 2,4-dibromo-5-methoxybenzenesulfonate, 2,2-dimethylpropyl 2,5-dibromo-4-methoxybenzenesulfonate, 2,2-dimethylpropyl 2,4-diiodo-5-methoxybenzenesulfonate, 2,2-dimethylpropyl 2,5-diiodo-4-methoxybenzenesulfonate and 1-(2,5-dichlorobenzenesulfonyl)pyrrolidine.

Among them, 2,2-dimethylpropyl 2,5-dichlorobenzenesulfonate, isobutyl 2,5-dichlorobenzenesulfonate, cyclohexyl 2,5-dichlorobenzenesulfonate, N,N-diethyl-2,5-dichlorobenzenesulfonamide and N-n-dodecyl-2,5-dichlorobenzenesulfonamide, 2,2-dimethylpropyl 2,5-dibromobenzenesulfonate, isobutyl 2,5-dibromobenzenesulfonate, cyclohexyl 2,5-dibromobenzenesulfonate, N,N-diethyl-2,5-dibromobenzenesulfonamide and N-n-dodecyl-2,5-dibromobenzenesulfonamide are preferable.

Specific examples of the aromatic compound (6) also include an aromatic compound represented by the formula (6):

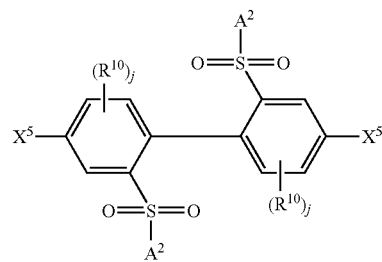

(6)

(hereinafter, simply referred to as the aromatic compound (6)).

In the formula (6), Examples of $A^2$ include the same as the above-mentioned $A^1$, and a C3-C20 unsubstituted alkoxy group is preferable, and an isopropyl group, an isobutoxy group, a 2,2-dimethylpropoxy group and a cyclohexyloxy group are more preferable.

Examples of the C1-C20 alkyl group, the C1-C20 alkoxy group, the C6-C20 aryl group, the C6-C20 aryloxy group and the C2-C20 acyl group in $R^{10}$ include the same as described above, respectively. As $R^{10}$, a C1-C20 unsubstituted alkyl group and a C1-C20 unsubstituted alkoxy group are preferable.

As $X^5$, a chlorine atom and a bromine atom are preferable and j is preferably 0.

Examples of the aromatic compound (6) include di(n-propyl) 4,4'-dichlorobiphenyl-2,2'-disulfonate, diisopropyl 4,4'-dichlorobiphenyl-2,2'-disulfonate, di(n-butyl) 4,4'-dichlorobiphenyl-2,2'-disulfonate, diisobutyl 4,4'-dichlorobiphenyl-2,2'-disulfonate, di(2,2-dimethylpropyl) 4,4'-dichlorobiphenyl-2,2'-disulfonate, dicyclohexyl 4,4'-dichlorobiphenyl-2,2'-disulfonate, di(n-octyl) 4,4'-dichlorobiphenyl-2,2'-disulfonate, di(n-pentadecyl) 4,4'-dichlorobiphenyl-2,2'-disulfonate, di(n-icosyl) 4,4'-dichlorobiphenyl-2,2'-disulfonate, N,N-diethyl-4,4'-dichlorobiphenyl-2,2'-disulfonamide, N,N-di(n-propyl)-4,4'-dichlorobiphenyl-2,2'-disulfonamide, N,N-diisopropyl-4,4'-dichlorobiphenyl-2,2'-disulfonamide, N,N-di(n-butyl)-4,4'-dichlorobiphenyl-2,2'-disulfonamide, N,N-diisobutyl-4,4'-dichlorobiphenyl-2,2'-disulfonamide, N-di(2,2-dimethylpropyl)-4,4'-dichlorobiphenyl-2,2'-disulfon amide, N-di(n-octyl)-4,4'-dichlorobiphenyl-2,2'-disulfonamide, N-di(n-dodecyl)-4,4'-dichlorobiphenyl-2,2'-disulfonamide, N,N-di(n-icosyl)-4,4'-dichlorobiphenyl-2,2'-disulfonamide, N,N-diphenyl-4,4'-dichlorobiphenyl-2,2'-disulfonamide, di(2,2-dimethylpropyl) 3,3'-dimethyl-4,4'-dichlorobiphenyl-2,2'-disulfonate, di(2,2-dimethylpropyl) 5,5'-dimethyl-4,4'-dichlorobiphenyl-2,2'-disulfonate, di(2,2-dimethylpropyl) 6,6'-dimethyl-4,4'-dichlorobiphenyl-2,2'-disulfonate, di(2,2-dimethylpropyl) 3,3'-dimethoxy-4,4'-dichlorobiphenyl-2,2'- disulfonate, di(2,2-dimethylpropyl) 5,5'-dimethoxy-4,4'-dichlorobiphenyl-2,2'-disulfonate, di(2,2-dimethylpropyl) 6,6'-dimethoxy-4,4'-dichlorobiphenyl-2,2'-disulfonate, di(2,2-dimethylpropyl) 3,3'-diphenyl-4,4'-dichlorobiphenyl-2,2'-disulfonate, di(2,2-dimethylpropyl) 3,3'-diacetyl-4,4'-dichlorobiphenyl-2,2'-disulfonate, di(2,2-dimethylpropyl) 5,5'-diacetyl-4,4'-dichlorobiphenyl-2,2'-disulfonate, di(n-propyl) 4,4'-dibromobiphenyl-2,2'-disulfonate, diisopropyl 4,4'-dibromobiphenyl-2,2'-disulfonate, di(n-butyl) 4,4'-dibromobiphenyl-2,2'-disulfonate, diisobutyl 4,4'-dibromobiphenyl-2,2'-disulfonate, di(2,2-dimethylpropyl) 4,4'-dibromobiphenyl-2,2'-disulfonate, dicyclohexyl 4,4'-dibromobiphenyl-2,2'-disulfonate, di(n-octyl) 4,4'-dibromobiphenyl-2,2'-disulfonate, di(n-pentadecyl) 4,4'-dibromobiphenyl-2,2'-disulfonate, di(n-icosyl) 4,4'-dibromobiphenyl-2,2'-disulfonate, N,N-diethyl-4,4'-dibromobiphenyl-2,2'-disulfonamide, N,N-di(n-propyl)-4,4'-dibromobiphenyl-2,2'-disulfonamide, N,N-diisopropyl-4,4'-dibromobiphenyl-2,2'-disulfonamide, N,N-di(n-butyl)-4,4'-dibromobiphenyl-2,2'-disulfonamide, N,N-diisobutyl-4,4'-dibromobiphenyl-2,2'-disulfonamide, N-di(2,2-dimethylpropyl)-4,4'-dibromobiphenyl-2,2'-disulfonamide, N-di(n-octyl)-4,4'-dibromobiphenyl-2,2'-disulfonamide, N-di(n-dodecyl)-4,4'-dibromobiphenyl-2,2'-disulfonamide, N-di(n-icosyl)-4,4'-dibromobiphenyl-2,2'-disulfonamide and N,N-diphenyl-4,4'-dibromobiphenyl-2,2'-disulfonamide.

Among them, diisopropyl 4,4'-dichlorobiphenyl-2,2'-disulfonate, di(2,2-dimethylpropyl) 4,4'-dichlorobiphenyl-2,2'-disulfonate, diisopropyl 4,4'-dibromobiphenyl-2,2'-disulfonate and di(2,2-dimethylpropyl) 4,4'-dibromobiphenyl-2,2'-disulfonate are preferable.

As the aromatic compound (4), a commercially available one may be used and one produced according to known methods may be used.

The aromatic compound (5) can be produced by reacting a compound represented by the formula (10):

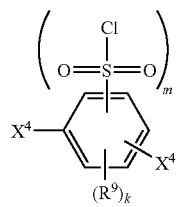

(10)

wherein $R^9$, $X^4$, m and k are the same meanings as described above (hereinafter, simply referred to as the compound (10)), with a compound represented by the formula (11):

$A^1$-H  (11)

wherein $A^1$ is the same meanings as described above (hereinafter, simply referred to as the compound (11)) in the presence of a tertiary amine compound or a pyridine compound according to the method described in WO07/043,274 A1.

Examples of the compound (10) include 2,5-dichlorobenzenesulfonyl chloride, 3,5-dichlorobenzenesulfonyl chloride, 2,5-dibromobenzenesulfonyl chloride and 3,5-dibromobenzenesulfonyl chloride. As the compound (10), a commercially available one is usually used.

Examples of the compound (11) include isopropanol, isobutanol, 2,2-dimethylpropanol, cyclohexanol, n-octanol, n-pentadecanol, n-icosanol, diethylamine, diisopropylamine, 2,2-dimethylpropylamine, n-dodecylamine and n-icosylamine. As the compound (11), a commercially available one is usually used.

The used amount of the compound (11) is usually 0.2 mole or more per 1 mole of the group represented by —$SO_2Cl$ in the compound (10) and there is no upper limit particularly. When the compound (11) is a liquid at the reaction temperature, large excess amount thereof may be used also to serve as the reaction solvent. The practical used amount of the compound (11) is 0.5 to 2 moles per 1 mole of the group represented by —$SO_2Cl$ in the compound (10).

Examples of the tertiary amine compound include trimethylamine, triethylamine, tri(n-propyl) amine, tri(n-butyl) amine, diisopropylethylamine, tri(n-octyl) amine, tri(n-decyl) amine, triphenylamine, N,N-dimethylaniline, N,N,N',N'-tetramethylethylenediamine and N-methylpyrrolidine. A commercially available tertiary amine compound is usually used. The used amount of the tertiary amine compound is usually 1 mole or more per 1 mole of the group represented by —$SO_2Cl$ in the compound (10) and there is no upper limit particularly. When the tertiary amine compound is a liquid at the reaction temperature, large excess amount thereof may be used also to serve as the reaction solvent. The practical used amount of the tertiary amine compound is 1 to 30 moles, preferably 1 to 20 moles and more preferably 1 to 10 moles per 1 mole of the group represented by —$SO_2Cl$ in the compound (10).

Examples of the pyridine compound include pyridine and 4-dimethylaminopyridine. A commercially available pyridine compound is usually used. The used amount of the pyridine compound is usually 1 mole or more per 1 mole of the group represented by —$SO_2Cl$ in the compound (10) and there is no upper limit particularly. When the pyridine compound is a liquid at the reaction temperature, large excess amount thereof may be used also to serve as the reaction solvent. The practical used amount of the pyridine compound is 1 to 30 moles, preferably 1 to 20 moles and more preferably 1 to 10 moles per 1 mole of the group represented by —$SO_2Cl$ in the compound (10).

The reaction of the compound (10) and the compound (11) is usually conducted by mixing the compound (10), the compound (11) and the tertiary amine compound or the pyridine compound in the presence of a solvent. The mixing order is not particularly limited.

Examples of the solvent include an aromatic hydrocarbon solvent such as toluene and xylene; an ether solvent such as diethyl ether, tetrahydrofuran and 1,4-dioxane; an aprotic polar solvent such as dimethylsulfoxide, N-methyl-2-pyrrolidone, N,N-dimethylformamide, N,N-dimethylacetamide and hexamethylphosphoric triamide; and a halogenated hydrocarbon solvent such as dichloromethane, chloroform, dichloroethane, chlorobenzene and dichlorobenzene. Alternatively, as described above, when the compound (11), the tertiary amine compound or the pyridine compound is a liquid at the reaction temperature, they may be used as a reaction solvent. The solvent may be used alone and two or more kinds thereof may be mixed to use. The used amount of the solvent is not particularly limited.

The temperature of the reaction of the compound (10) and the compound (11) is usually −30 to 150° C. and preferably −10 to 70° C. The reaction time is usually 0.5 to 24 hours.

After completion of the reaction, for example, an organic layer containing the aromatic compound (5) can be obtained by adding water or an aqueous acid solution and if necessary, a water-insoluble organic solvent such as an aromatic hydrocarbon solvent such as toluene and xylene; an aliphatic hydrocarbon solvent such as hexane and heptane; a halogenated hydrocarbon solvent such as dichloromethane, dichloroethane and chloroform; and an ester solvent such as ethyl acetate to the reaction mixture followed by conducting an extraction. The aromatic compound (5) can be isolated by concentrating the obtained organic layer, if necessary, after washing it with water, an aqueous alkali solution or the like.

The aromatic compound (6) can be produced according to the same manner as the above-mentioned process for producing the aromatic compound (5), except that a compound represented by the formula (12):

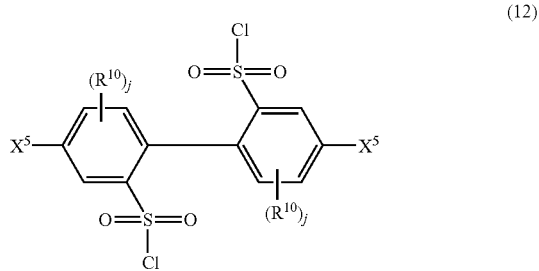

(12)

wherein $R^{10}$, $X^5$ and j are the same meanings as defined above (hereinafter, simply referred to as the compound (12)) is used in place of the compound (10) and a compound represented by the formula (13):

(13)

wherein $A^2$ is the same meaning as defined above (hereinafter simply referred to as the compound (13)) is used in place of the compound (11).

Examples of the compound (12) include 4,4'-dichlorobiphenyl-2,2'-disulfonyl dichloride, 4,4'-dibromobiphenyl-2,2'-disulfonyl dichloride, 3,3'-dimethyl-4,4'-dichlorobiphenyl-2,2'-disulfonyl dichloride, 5,5'-dimethyl-4,4'-dichlorobiphenyl-2,2'-disulfonyl dichloride, 6,6'-dimethyl-4,4'-dichlorobiphenyl-2,2'-disulfonyl dichloride, 3,3'-dimethoxy-4,4'-dichlorobiphenyl-2,2'-disulfonyl dichloride, 5,5'-dimethoxy-4,4'-dichlorobiphenyl-2,2'-disulfonyl dichloride, 6,6'-dimethoxy-4,4'-dichlorobiphenyl-2,2'-disulfonyl dichloride, 3,3'-diphenyl-4,4'-dichlorobiphenyl-2,2'-disulfonyl dichloride, 3,3'-diacetyl-4,4'-dichlorobiphenyl-2,2'-disulfonyl dichloride, 5,5'-diacetyl-4,4'-dichlorobiphenyl-2,2'-disulfonyl dichloride, and 6,6'-diacetyl-4,4'-dichlorobiphenyl-2,2'-disulfonyl dichloride, and 4,4'-dichlorobiphenyl-2,2'-disulfonyl dichloride and 4,4'-dibromobiphenyl-2,2'-disulfonyl dichloride are preferable. As the compound (12), a commercially available one may be used, and one produced according to known methods described in, for example, Bull. Soc. Chim. Fr., 4, 49 (1931), 1047-1049 may be used.

Examples of the compound (13) include the same as the compound (11) and a commercially available one is usually used.

Specific examples of the aromatic compound also include an aromatic compound represented by the formula (7):

(hereinafter, simply referred to as the aromatic compound (7)).

In the formula (7), n is preferably an integer of 5 or more, and more preferably an integer of 10 or more.

Examples of the divalent aromatic group in $Ar^2$, $Ar^3$, $Ar^4$ and $Ar^5$ include a divalent monocyclic aromatic group such as a 1,3-phenylene group, a 1,4-phenylene group and 4,4'-biphenyl-1,1'-diyl group; a divalent condensed aromatic group such as a naphthalene-1,3-diyl group, a naphthalene-1,4-diyl group, a naphthalene-1,5-diyl group, a naphthalene-1,6-diyl group, a naphthalene-1,7-diyl group, a naphthalene-2,6-diyl group, a naphthalene-2,7-diyl group and a 9H-fluorene-2,7-diyl group; and a divalent heteroaromatic group such as a pyridine-2,5-diyl group, a pyridine-2,6-diyl group, a quinoxaline-2,6-diyl group, a thiophene-2,5-diyl group, 2,2'-bithiophene-5,5'-diyl group, a pyrrole-2,5-diyl group, a 2,2'-bipyridine-5,5'-diyl group, a pyrimidine-2,5-diyl group, a quinoline-5,8-diyl group, a quinoline-2,6-diyl group, an isoquinoline-1,4-diyl group, an isoquinoline-5,8-diyl group, 2,1,3-benzothiadiazole-4,7-diyl group, a benzimidazole-4,7-diyl group, a quinoxaline-5,8-diyl group and a quinoxaline-2,6-diyl group. Among them, the divalent monocyclic aromatic group and the divalent condensed aromatic group are preferable, and a 1,4-phenylene group, a naphthalene-1,4-diyl group, a naphthalene-1,5-diyl group, a naphthalene-2,6-diyl group and a naphthalene-2,7-diyl group are more preferable.

The divalent aromatic group may be substituted with at least one substituent selected from the group consisting of the following (a2) to (e2).

(a2) a C1-C20 alkyl group which may be substituted with at least one substituent selected from the group consisting of a fluorine atom, a cyano group, a C1-C20 alkoxy group, a C6-C20 aryl group and a C6-C20 aryloxy group;

(b2) a C1-C20 alkoxy group which may be substituted with at least one substituent selected from the group consisting of a fluorine atom, a cyano group, a C1-C20 alkoxy group, a C6-C20 aryl group and a C6-C20 aryloxy group;

(c2) a C6-C20 aryl group which may be substituted with at least one substituent selected from the group consisting of a fluorine atom, a cyano group, a C1-C20 alkoxy group and a C6-C10 aryloxy group;

(d2) a C6-C20 aryloxy group which may be substituted with at least one substituent selected from the group consisting of a fluorine atom, a cyano group, a C1-C20 alkoxy group and a C6-C20 aryloxy group; and (e2) a C2-C20 acyl group which may be substituted with at least one substituent selected from the group consisting of a fluorine atom, a cyano group, a C1-C20 alkoxy group, a C6-C20 aryl group and a C6-C20 aryloxy group.

Examples of the C1-C20 alkoxy group, the C6-C20 aryl group, the C6-C20 aryloxy group, the C1-C20 alkyl group and the C2-C20 acyl group in (a2) to (e2) include the same as described above.

Examples of (a2) include the same as the above-mentioned (a1). Examples of (b2) include the same as the above-mentioned (b1). Examples of (c2) include the same as the above-mentioned (c1). Examples of (d2) include the same as the above-mentioned (d1). Examples of (e2) include the same as the above-mentioned (e1).

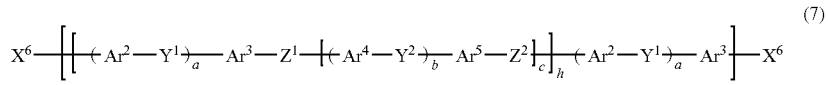

(7)

As $X^6$, a chlorine atom and a bromine atom are preferable.
Specific examples of the aromatic compound (7) include the following compounds and the following compounds wherein both terminal chlorine atoms are replaced to bromine atoms. Additionally, in the following formulae, h is the same meanings as the above.
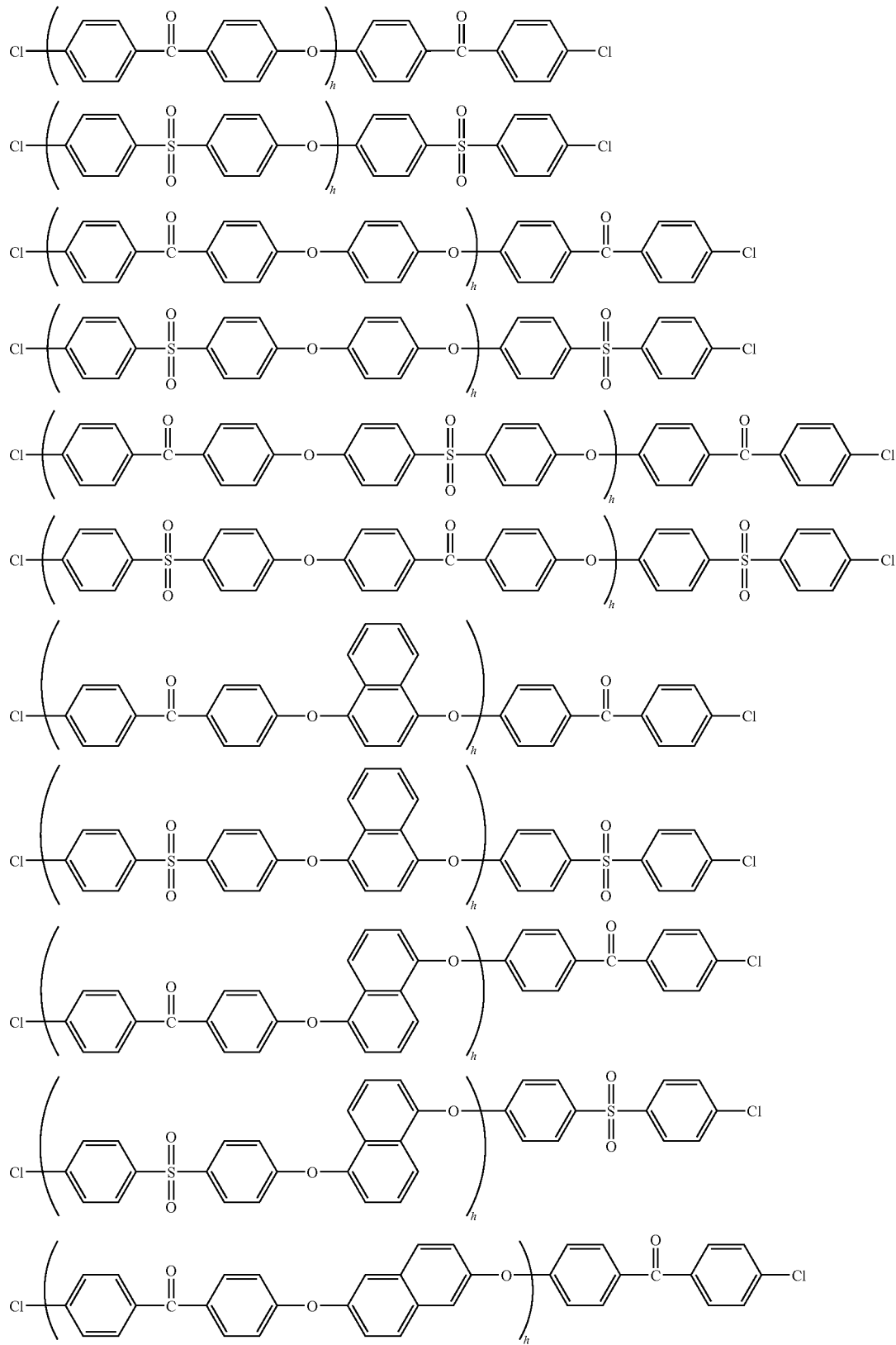

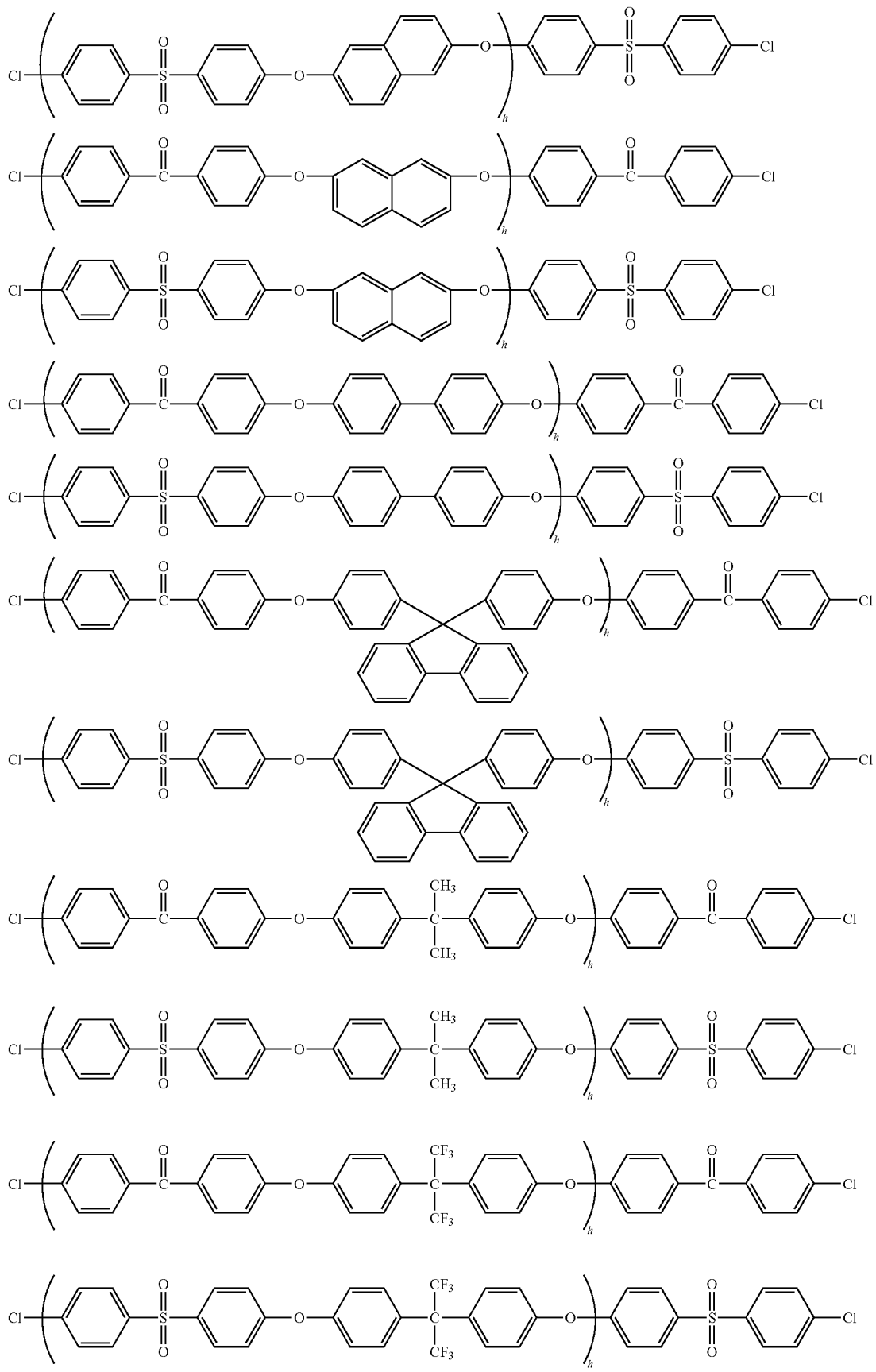

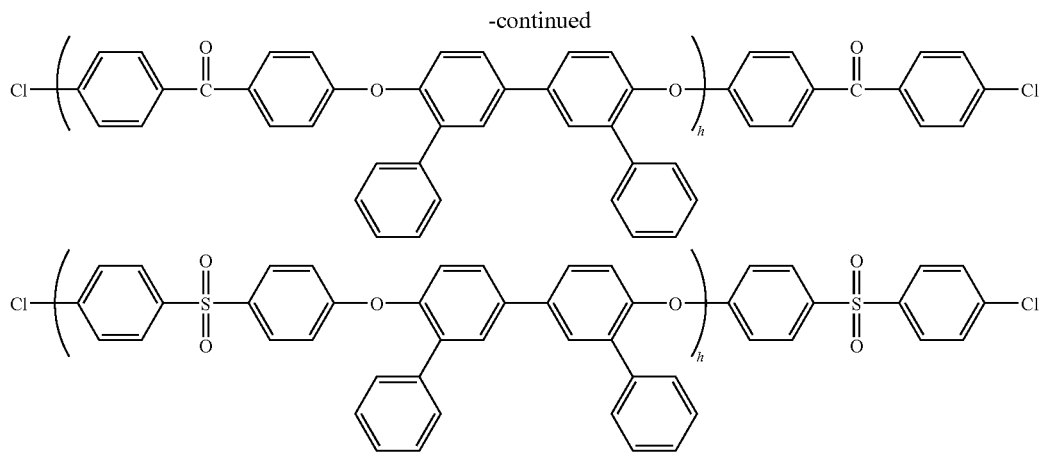

As the aromatic compound (7), one produced according to known methods such as JP Patent No. 2,745,727 may be used and a commercially available one may be used. Examples of the commercially available one include SUMIKA EXCEL PES manufactured by Sumitomo Chemical Company, Limited.

As the aromatic compound (7), one having 2,000 or more of weight average molecular weight equivalent to polystyrene is preferably used, and one having 3,000 or more of weight average molecular weight equivalent to polystyrene is more preferable.

The method for production of a conjugated aromatic compound of the present invention comprises reacting an aromatic compound (A) with an aromatic compound (A) having the same structure as that of the above-mentioned aromatic compound (A) or an aromatic compound (B) being structurally different from the above-mentioned aromatic compound (A).

In the present specification, conjugated aromatic compound means a compound having at least one aromatic ring and possessing a delocated π-electron system in a part of or all of its molecule.

Specific examples of cases where an aromatic compound (A) is reacted with an aromatic compound (A) having the same structure as that of the above-mentioned aromatic compound (A) include
a case where an aromatic compound (4) is used as the aromatic compound (A);
a case where an aromatic compound (5) is used as the aromatic compound (A); and
a case where an aromatic compound (6) is used as the aromatic compound (A).

Specific examples of cases where an aromatic compound (A) is reacted with an aromatic compound (B) being structurally different from the above-mentioned aromatic compound (A) include a case where an aromatic compound (4) is used as the aromatic compound (A) and an aromatic compound (4) being structurally different from the above-mentioned aromatic compound (A) is used as the aromatic compound (B);
a case where an aromatic compound (4) is used as the aromatic compound (A) and an aromatic compound (5) being structurally different from the above-mentioned aromatic compound (A) is used as the aromatic compound (B);
a case where an aromatic compound (4) is used as the aromatic compound (A) and an aromatic compound (6) being structurally different from the above-mentioned aromatic compound (A) is used as the aromatic compound (B);
a case where an aromatic compound (4) is used as the aromatic compound (A) and an aromatic compound (7) being structurally different from the above-mentioned aromatic compound (A) is used as the aromatic compound (B);
a case where an aromatic compound (5) is used as the aromatic compound (A) and an aromatic compound (4) being structurally different from the above-mentioned aromatic compound (A) is used as the aromatic compound (B);
a case where an aromatic compound (5) is used as the aromatic compound (A) and an aromatic compound (5) being structurally different from the above-mentioned aromatic compound (A) is used as the aromatic compound (B);
a case where an aromatic compound (5) is used as the aromatic compound (A) and an aromatic compound (6) being structurally different from the above-mentioned aromatic compound (A) is used as the aromatic compound (B);
a case where an aromatic compound (5) is used as the aromatic compound (A) and an aromatic compound (7) being structurally different from the above-mentioned aromatic compound (A) is used as the aromatic compound (B);
a case where an aromatic compound (6) is used as the aromatic compound (A) and an aromatic compound (4) being structurally different from the above-mentioned aromatic compound (A) is used as the aromatic compound (B);
a case where an aromatic compound (6) is used as the aromatic compound (A) and an aromatic compound (5) being structurally different from the above-mentioned aromatic compound (A) is used as the aromatic compound (B);
a case where an aromatic compound (6) is used as the aromatic compound (A) and an aromatic compound (6) being structurally different from the above-mentioned aromatic compound (A) is used as the aromatic compound (B); and
a case where an aromatic compound (6) is used as the aromatic compound (A) and an aromatic compound (7) being structurally different from the above-mentioned aromatic compound (A) is used as the aromatic compound (B).

The used transition metal complex is a transition metal complex obtained by contacting a compound of a transition metal belonging to Group 9, 10 or 11 with the bipyridine compound (1), and a transition metal complex obtained by contacting a compound of a transition metal belonging to Group 10 with the bipyridine compound (1) is preferable and a transition metal complex obtained by contacting a nickel compound with the bipyridine compound (1) is more preferable.

When the used amount of the transition metal complex is too small, a conjugated aromatic compound having a small molecular weight tends to be obtained or a yield of a conjugated aromatic compound tends to be low, and when the used amount of the transition metal complex is too much, the aftertreatment after the completion of reaction tends to be cumbersome although a conjugated aromatic compound having a large molecular weight tends to be obtained or a yield of a conjugated aromatic compound tends to be high. Therefore, the practical used amount of the transition metal complex is usually 0.001 to 1 mole per 1 mole of all of used aromatic compound in terms of a transition metal.

As necessary, a reducing agent may be used, and a kind of the reducing agent and the used amount of the reducing agent are accordingly selected depending on kinds and the amounts of the used transition metal complex and the aromatic compounds. Examples of the reducing include metals such as zinc, magnesium, manganese, aluminum and sodium, and zinc, magnesium and manganese are preferable. When the reducing agent is used, the used amount thereof is usually 1 to 10 moles and preferably 1 to 5 moles per 1 mole of all of the aromatic compounds used.

The reaction is usually carried out in the presence of a solvent. The solvent may be one in which the used aromatic compounds and the produced conjugated aromatic compound can be dissolved. Specific examples of the solvent include an aromatic hydrocarbon solvent such as toluene and xylene; an ether solvent such as tetrahydrofuran and 1,4-dioxane; an aprotic polar solvent such as dimethylsulfoxide, N-methylpyrrolidone, N,N-dimethylformamide, N,N-dimethylacetamide and hexamethylphosphoric triamide; and a halogenated hydrocarbon solvent such as dichloromethane and dichloroethane. These solvents may be used alone, and two or more thereof may be mixed to use. Among them, the ether solvent and the aprotic polar solvent are preferable and tetrahydrofuran, dimethylsulfoxide, N-methyl-2-pyrrolidone and N,N-dimethylacetamide are more preferable. When the used amount of the solvent is too much, a conjugated aromatic compound having small molecular weight tends to be obtained or a yield of a conjugated aromatic compound tends to be low, and when the used amount thereof is too small, the property of the reaction mixture tends to be bad, and therefore, the practical used amount thereof is 1 to 200 parts by weight and preferably 5 to 100 parts by weight per 1 parts by weight of all of the aromatic compounds used.

The reaction is usually conducted by mixing the solvent, the aromatic compounds, the transition metal complex and if necessary, the reducing agent in an atmosphere of an inert gas such as nitrogen gas. The reaction may be carried out together with a preparation of the transition metal complex by mixing the solvent, the aromatic compounds, the compound of a transition metal belonging to Group 9, 10 or 11 and the bipyridine compound (1).

The reaction temperature is usually 0 to 250° C. and preferably 30 to 100° C. The reaction time is usually 0.5 to 48 hours.

When the produced conjugated aromatic compound is a polymer, for example, after completion of the reaction, the conjugated aromatic compound is precipitated by mixing a solvent in which the produced conjugated aromatic compound is not soluble or is poorly soluble with the reaction mixture to precipitate the conjugated aromatic compound followed by filtration, thereby being able to separate the precipitated conjugated aromatic compound from the reaction mixture. A solvent in which the produced conjugated aromatic compound is not soluble or is poorly soluble is mixed with the reaction mixture and then adding an aqueous acid solution such as hydrochloric acid thereto and the precipitated conjugated aromatic compound may be separated from the reaction mixture by filtration. The molecular weight and structure of the obtained conjugated aromatic compound can be analyzed by a conventional means such as gel permeation chromatography and NMR. Examples of the solvent in which the produced conjugated aromatic compound is not soluble or is poorly soluble include water, methanol, ethanol and acetonitrile, and water and methanol are preferable.

When the produced conjugated aromatic compound is not a polymer, for example, after completion of the reaction, the produced conjugated aromatic compound can be isolated by concentrating the reaction mixture. The isolated conjugated aromatic compound may be further purified by a conventional purification means such as column chromatography, distillation and recrystallization.

The specific examples of the obtained conjugated aromatic compound are shown below.

In a case where an aromatic compound (A) is reacted with an aromatic compound (A) having the same structure as that of the above-mentioned aromatic compound (A) and the aromatic compound (4) wherein n is 1 is used as the aromatic compound (A), the conjugated aromatic compound represented by the following formula (20):

$$Ar^1\text{---}Ar^1 \qquad (20)$$

wherein $Ar^1$ is the same meaning as defined above, is obtained.

Examples of the conjugated aromatic compound represented by the following formula (20) include biphenyl, 4,4'-difluorobiphenyl, 3,3'-difluorobiphenyl, 2,2'-difluorobiphenyl, 2,2'-dimethylbiphenyl, 2,2',5,5'-tetramethylbiphenyl, 2,2'-diethylbiphenyl, 3,3'-di-n-propylbiphenyl, 4,4'-diisopropylbiphenyl, 5,5'-di-n-butylbiphenyl, 2,2'-diisobutylbiphenyl, 3,3'-di-sec-butylbiphenyl, 4,4'-di-tert-butylbiphenyl, 5,5'-bis(2,2-dimethylpropyl)biphenyl, 2,2'-di-n-hexylbiphenyl, 4,4'-dicyclohexylbiphenyl, 4,4'-dibenzylbiphenyl, 4,4'-dicyanobiphenyl, 4,4'-bis(trifluoromethyl)biphenyl, 2,2'-bis(trifluoromethyl)biphenyl, 4,4'-bis(cyanomethyl)biphenyl, 3,3'-dimethoxybiphenyl, 4,4'-dimethoxybiphenyl, 2,2',3,3'-tetramethoxybiphenyl, 2,2',4,4'-tetramethoxybiphenyl, 2,2',5,5'-tetramethoxybiphenyl, 2,2'-diethoxybiphenyl, 3,3'-di-n-propoxybiphenyl, 4,4'-diisopropoxybiphenyl, 5,5'-di-n-butoxybiphenyl, 4,4'-di-tert-butoxybiphenyl, 4,4'-diphenoxybiphenyl, 4,4'-dibenzyloxybiphenyl, 4,4'-bis(methoxymethyl)biphenyl, 4,4'-bis(n-butoxymethyl)biphenyl, 4,4'-bis(methoxymethoxy)biphenyl, 4,4'-bis(benzyloxymethoxy)biphenyl, 4,4'-bis{2-(n-butoxy)ethoxy}biphenyl, 4,4'-diacetylbiphenyl, 4,4'-dibenzoylbiphenyl, 4,4'-bis(phenylsulfonyl)biphenyl, dimethyl biphenyl-4,4'-disulfonate, diethyl biphenyl-4,4'-disulfonate, di(2,2-dimethylpropyl)biphenyl-4,4'-disulfonate, di(2,2-dimethylpropyl)biphenyl-3,3'-disulfonate, 1,1'-binaphthalene, 2,2'-bithiophene, 3,3'-dihexyl-5,5'-bithiophene, 1,1'-dimethyl-5,5'-bipyrrole, 2,2'-bipyridine, 3,3'-dimethyl-2,2'-bipyridine, 3,3'-dihexyl-5,5'-bipyridine, 2,2'-bipyrimidine, 5,5'-biquinoline, 1,1'-biisoquinoline, 4,4'-bis(2,1,3-benzothiadiazole) and 7,7'-bis(benzimidazole).

In a case where an aromatic compound (A) is reacted with an aromatic compound (A) having the same structure as that of the above-mentioned aromatic compound (A) and the aromatic compound (4) wherein n is 2 is used as the aromatic compound (A), the conjugated aromatic compound having a repeating unit represented by the following formula (21):

$$\text{---}(A^1)\text{---} \qquad (21)$$

wherein $Ar^1$ is the same meaning as defined above, is obtained. The conjugated aromatic compound usually contains 2 to 10,000 of the repeating unit represented by the formula (21), and the weight average molecular weight thereof equivalent to polystyrene is usually 500 to 3,000,000.

Specific examples of the repeating unit represented by the formula (21) include the repeating units represented by the following formulae (21a) to (21d).

(21a)

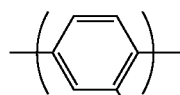
(21b)

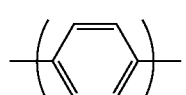
(21c)

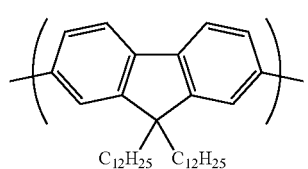
(21d)

In a case where an aromatic compound (A) is reacted with an aromatic compound (A) having the same structure as that of the above-mentioned aromatic compound (A) and the aromatic compound (5) is used as the aromatic compound (A), the conjugated aromatic compound having a repeating unit represented by the following formula (22):

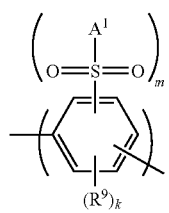
(22)

wherein $Ar^1$, $R^9$, k and m are the same meanings as defined above, is obtained. The conjugated aromatic compound usually contains 2 to 10,000 of the repeating unit represented by the formula (22), and the weight average molecular weight thereof equivalent to polystyrene is usually 500 to 3,000,000.

Specific examples of the repeating unit represented by the formula (22) include the repeating units represented by the following formulae (22a) to (22e).

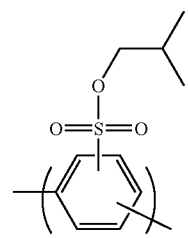
(22a)

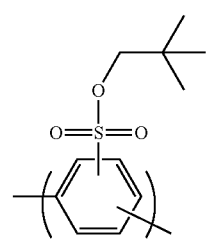
(22b)

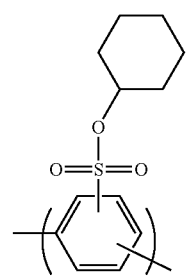
(22c)

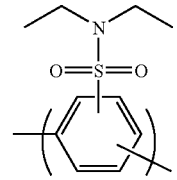
(22d)

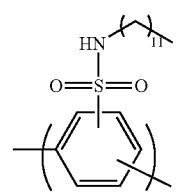
(22e)

In a case where an aromatic compound (A) is reacted with an aromatic compound (A) having the same structure as that of the above-mentioned aromatic compound (A) and the aromatic compound (6) is used as the aromatic compound (A), the conjugated aromatic compound having a repeating unit represented by the following formula (23):

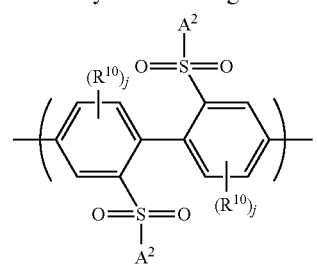
(23)

is obtained. The conjugated aromatic compound usually contains 2 to 10,000 of the repeating unit represented by the formula (23), and the weight average molecular weight thereof equivalent to polystyrene is usually 1,000 to 6,000,000.

Specific examples of the repeating unit represented by the formula (23) include the repeating units represented by the following formulae (23a) to (23e).

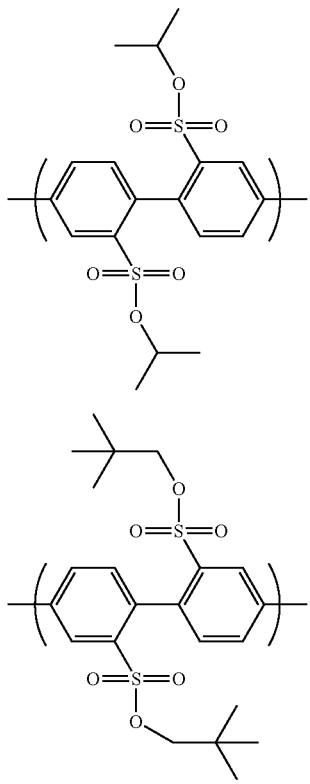

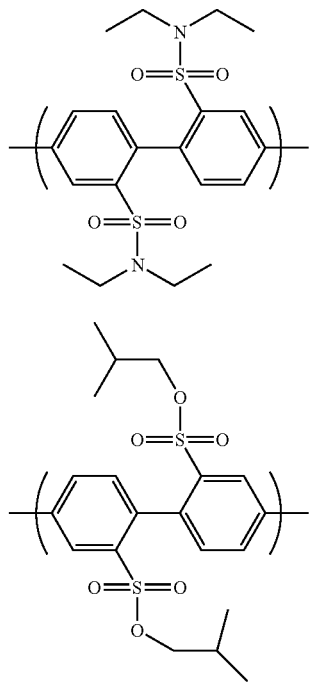

In a case where an aromatic compound (A) is reacted with an aromatic compound (B) being structurally different from the above-mentioned aromatic compound (A) and the aromatic compound (4) wherein n is 2 is used as the aromatic compound (A) and the aromatic compound (7) is used as the aromatic compound (B), a conjugated aromatic compound comprising the above-mentioned repeating unit represented by the formula (21) and a segment represented by the following formula (24):

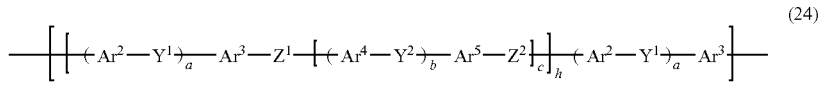

is obtained. The weight average molecular weight thereof equivalent to polystyrene of the conjugated aromatic compound is usually 3,000 to 3,000,000.

Specific examples of the segment represented by the formula (24) include the following segments represented by the formulae (24a) to (24x). Additionally, in the following formulae, h represents the same meaning as defined above and is preferably an integer of 5 or more and more preferably an integer of 10 or more.

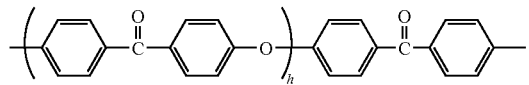

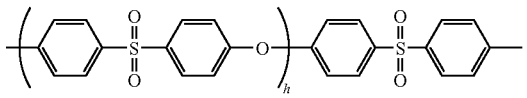

-continued
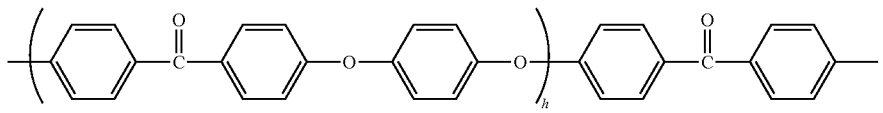
(24c)
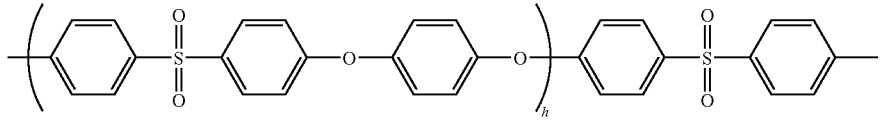
(24d)
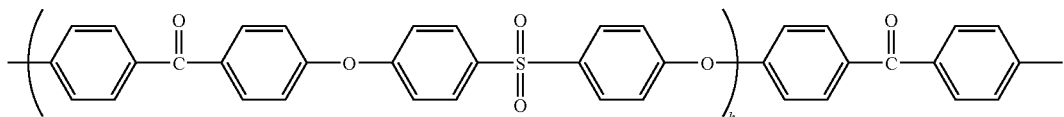
(24e)
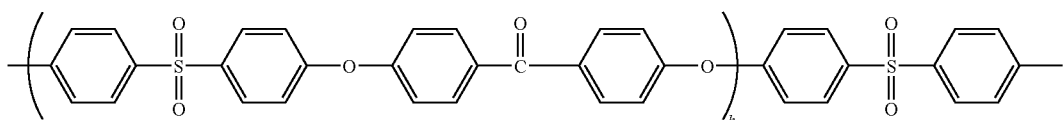
(24f)
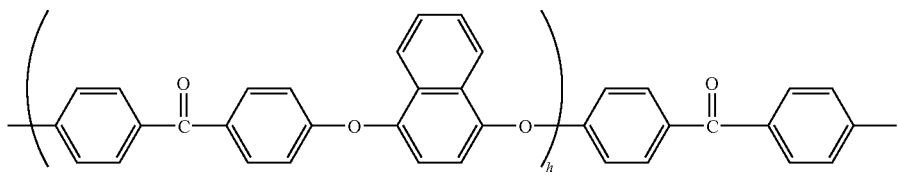
(24g)
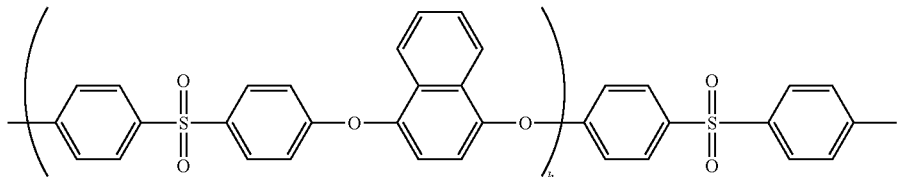
(24h)
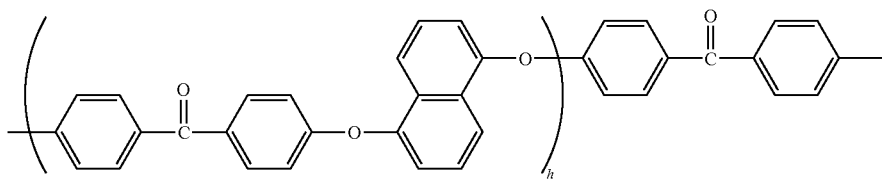
(24i)
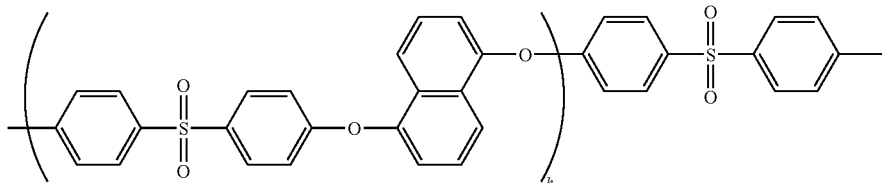
(24j)
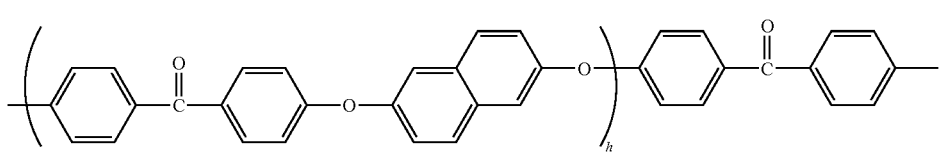
(24k)
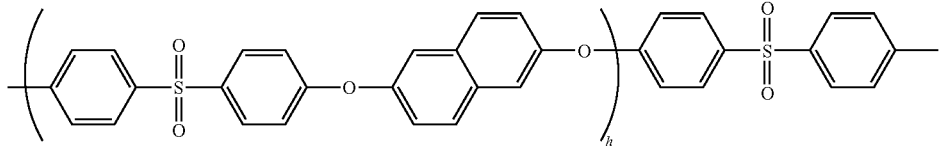
(24l)

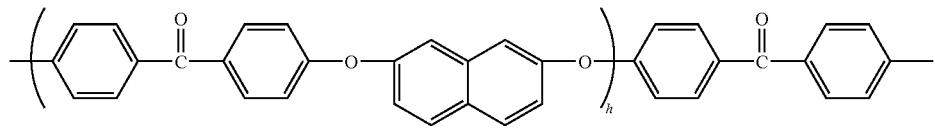
(24m)
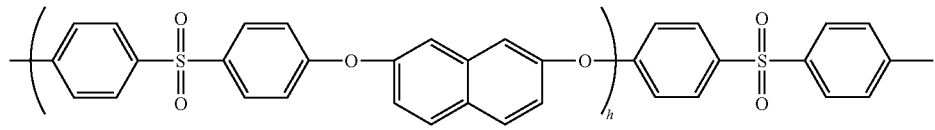
(24n)
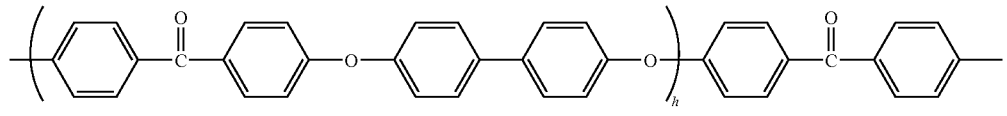
(24o)
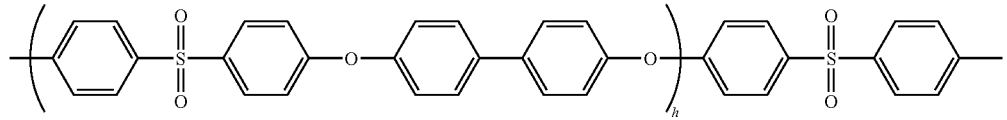
(24p)
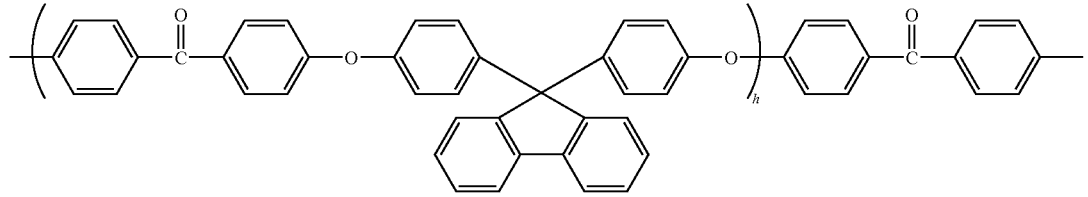
(24q)
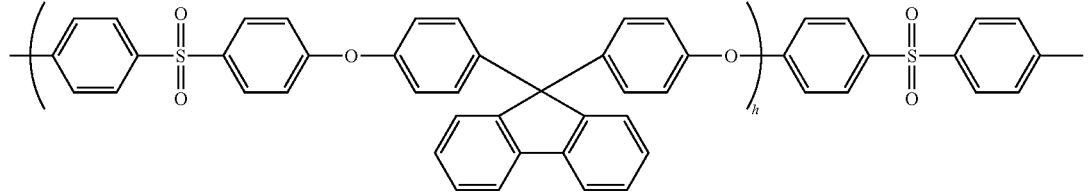
(24r)
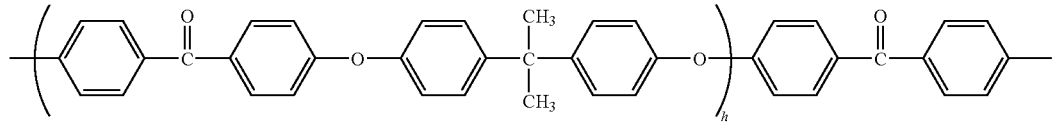
(24s)
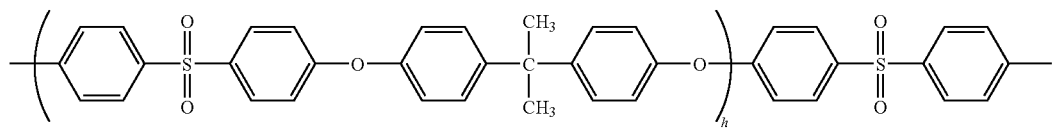
(24t)
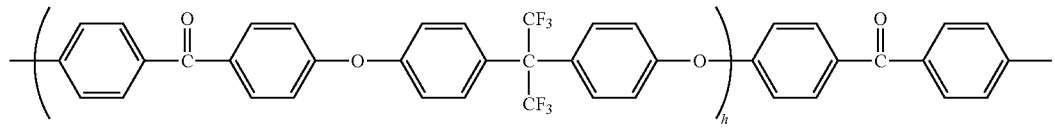
(24u)
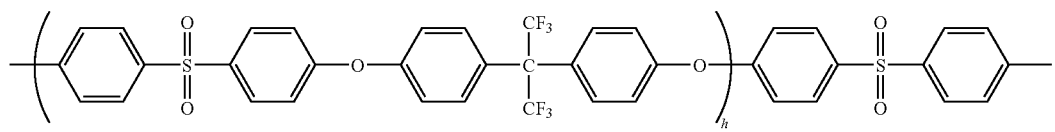
(24v)

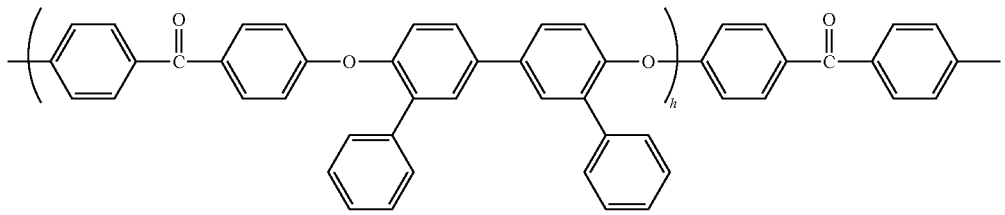
(24w)

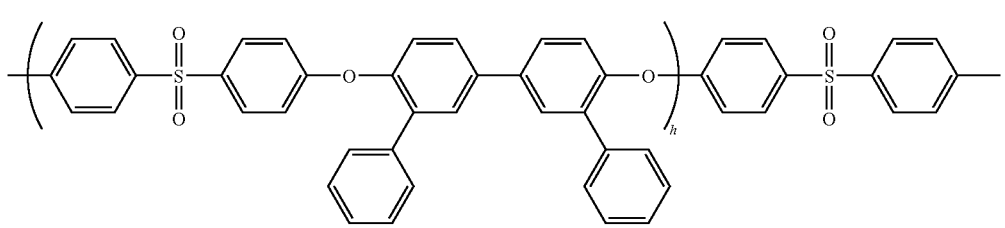
(24x)

Examples of the conjugated aromatic compound comprising the repeating unit represented by the formula (21) and the segment represented by the formula (24) include a conjugated aromatic compound comprising any one repeating unit of the above-mentioned repeating units represented by the formulae (21a) to (21d) and any one segment of the above-mentioned segments represented by the formulae (24a) to (24x). Specifically, the following conjugated aromatic compounds represented by the formulae (I-1) to (I-16) are listed. Herein, in the following formulae, h represents the same meaning as defined above, and p represents an integer of 2 or more.

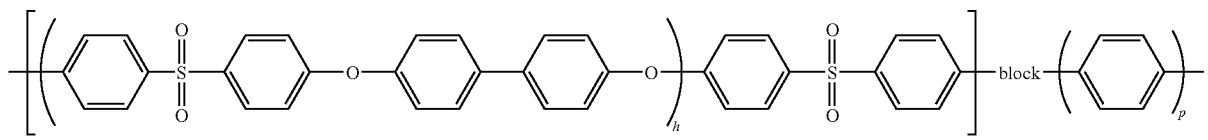
(I-1)

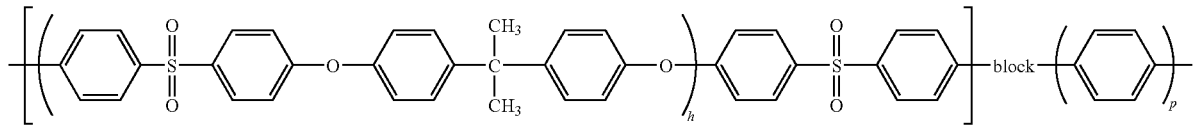
(I-2)

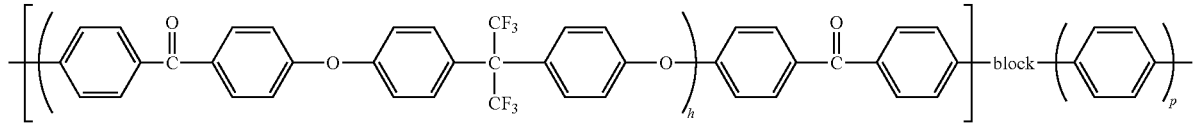
(I-3)

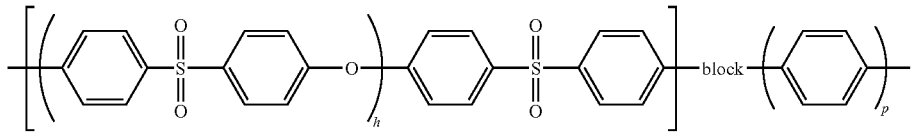
(I-4)

(I-5)
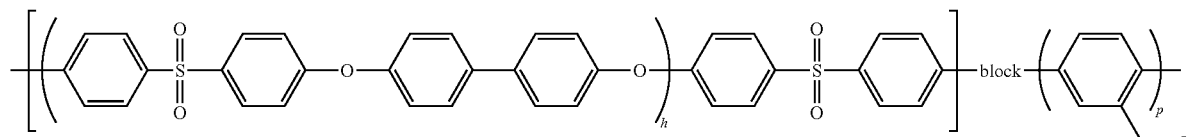
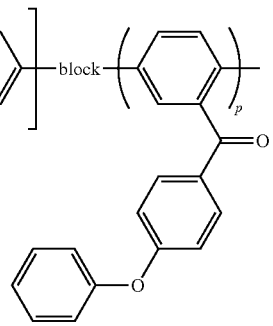
(I-6)
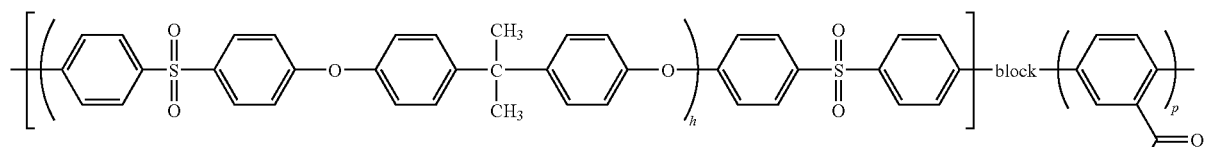
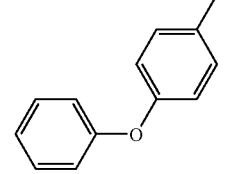
(I-7)
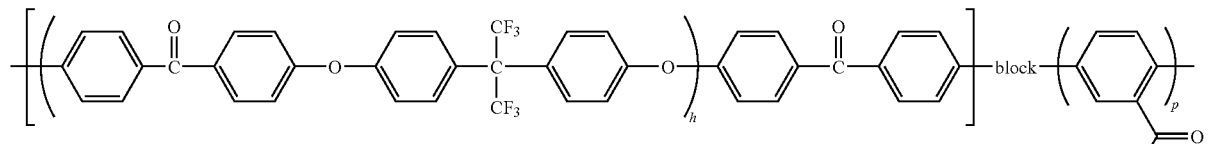
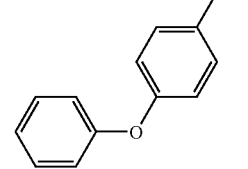
(I-8)
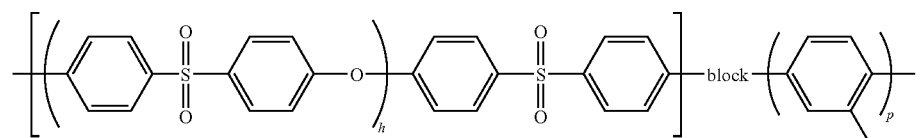
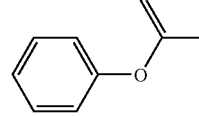
(I-9)
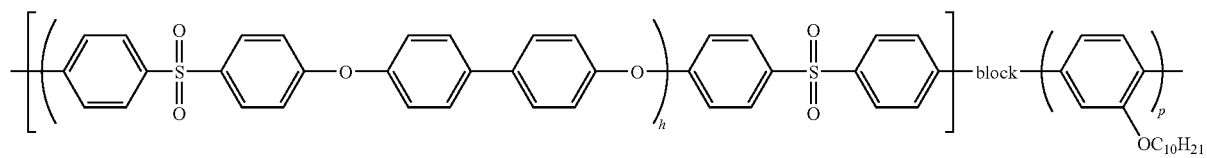

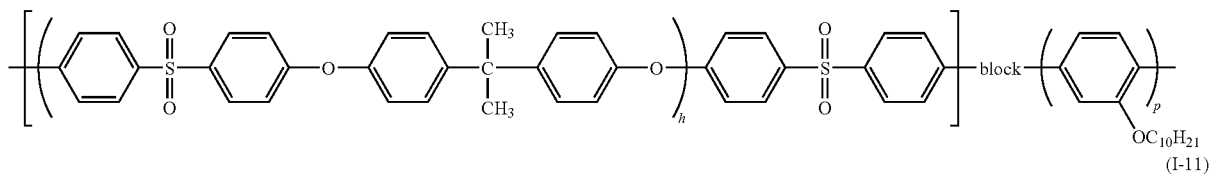
(I-10)

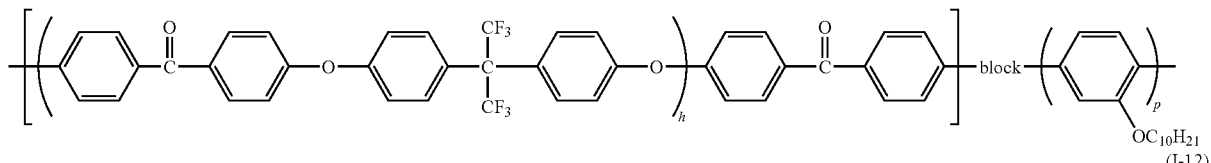
(I-11)

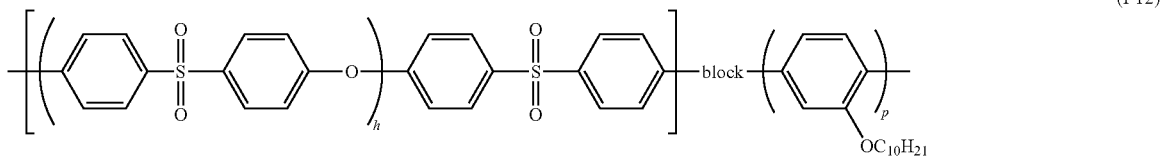
(I-12)

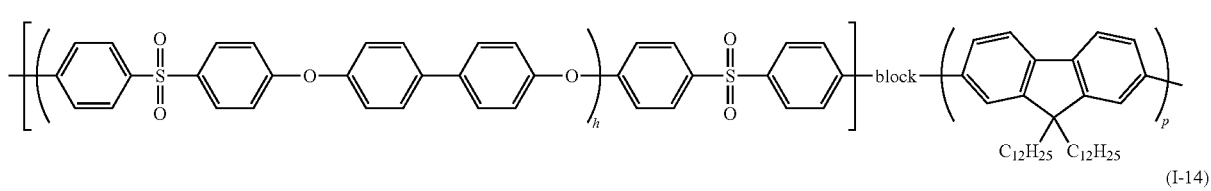
(I-13)

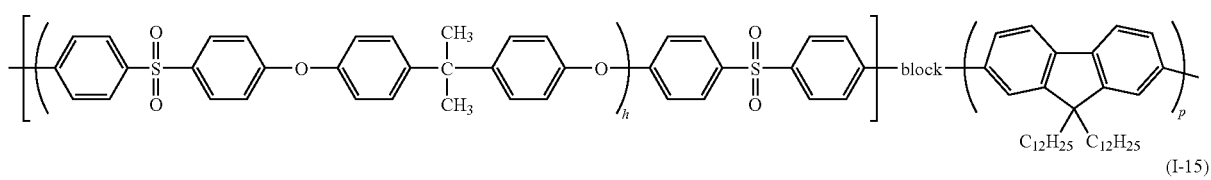
(I-14)

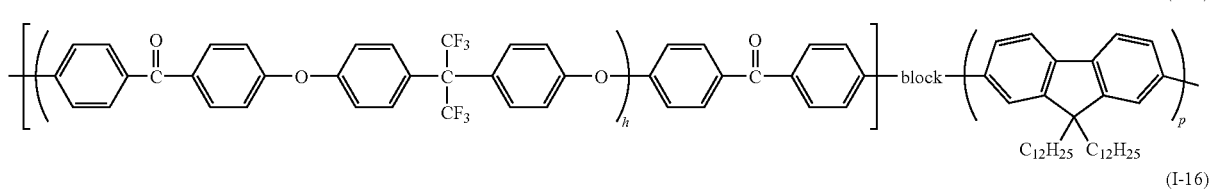
(I-15)

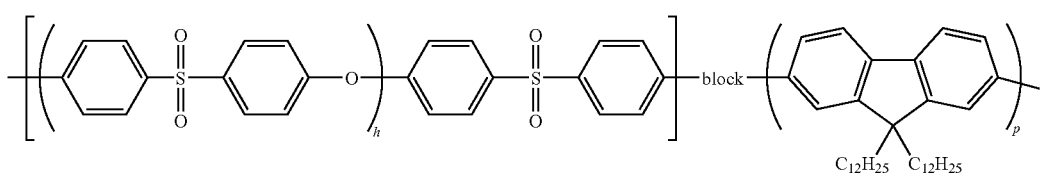
(I-16)

In a case where an aromatic compound (A) is reacted with an aromatic compound (B) being structurally different from the above-mentioned aromatic compound (A) and the aromatic compound (5) is used as the aromatic compound (A) and the aromatic compound (7) is used as the aromatic compound (B), a conjugated aromatic compound comprising the above-mentioned repeating unit represented by the formula (22) and a segment represented by the following formula (24) is obtained. The weight average molecular weight thereof equivalent to polystyrene of the conjugated aromatic compound is usually 3,000 to 3,000,000. The amount of the repeating unit represented by the formula (22) in the conjugated aromatic compound is preferably 5% by weight or more and 95% by weight or less, and more preferably 30% by weight or more and 90% by weight or less, and the amount of the segment represented by the formula (24) is preferably 5% by weight or more and 95% by weight or less, and more preferably 10% by weight or more and 70% by weight or less.

Examples of the conjugated aromatic compound comprising the repeating unit represented by the formula (22) and the segment represented by the formula (24) include a conjugated aromatic compound comprising any one repeating unit of the above-mentioned repeating units represented by the formulae (22a) to (22e) and any one segment of the above-mentioned segments represented by the formulae (24a) to (24x). Specifically, the following conjugated aromatic compounds represented by the formulae (II-1) to (II-9) are listed. Herein, in the following formulae, h and p represents the same meanings as defined above.

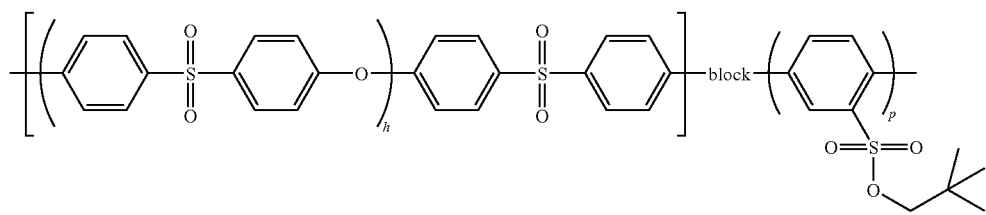
(II-1)
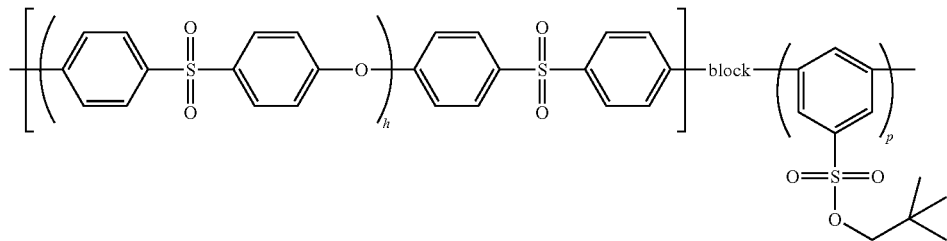
(II-2)
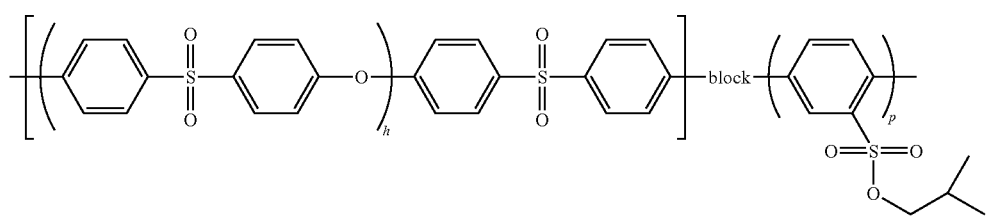
(II-3)
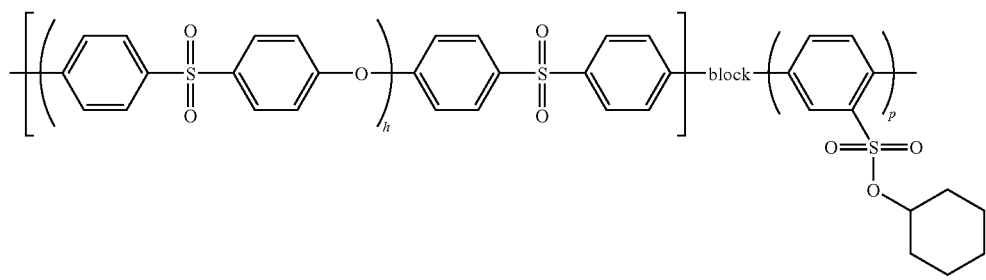
(II-4)
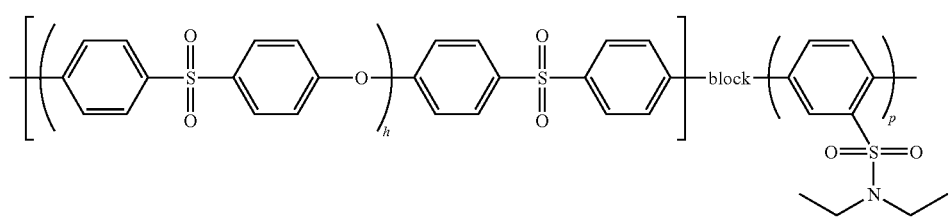
(II-5)
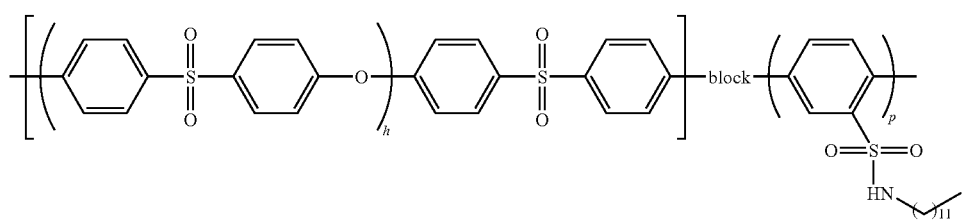
(II-6)
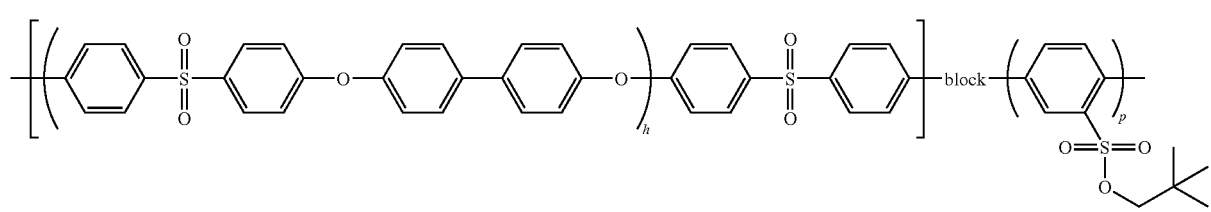
(II-7)

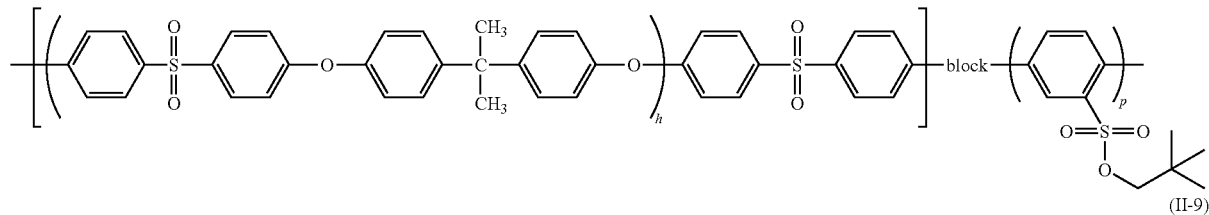

(II-8)

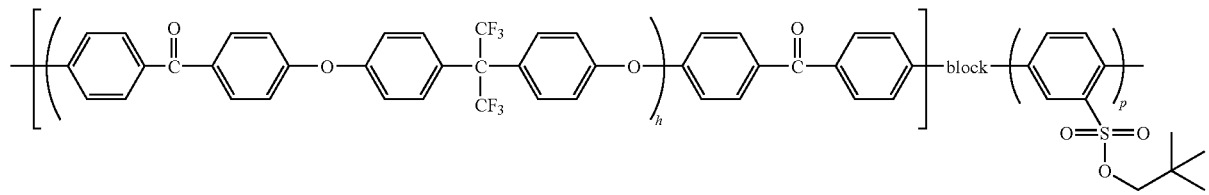

(II-9)

In a case where an aromatic compound (A) is reacted with an aromatic compound (B) being structurally different from the above-mentioned aromatic compound (A) and the aromatic compound (6) is used as the aromatic compound (A) and the aromatic compound (7) is used as the aromatic compound (B), a conjugated aromatic compound comprising the above-mentioned repeating unit represented by the formula (23) and a segment represented by the following formula (24) is obtained. The weight average molecular weight thereof equivalent to polystyrene of the conjugated aromatic compound is usually 3,000 to 3,000,000. The amount of the repeating unit represented by the formula (23) in the conjugated aromatic compound is preferably 5% by weight or more and 95% by weight or less, and more preferably 30% by weight or more and 90% by weight or less, and the amount of the segment represented by the formula (24) is preferably 5% by weight or more and 95% by weight or less, and more preferably 10% by weight or more and 70% by weight or less.

Examples of the conjugated aromatic compound comprising the repeating unit represented by the formula (23) and the segment represented by the formula (24) include a conjugated aromatic compound comprising any one repeating unit of the above-mentioned repeating units represented by the formulae (23a) to (23d) and any one segment of the above-mentioned segments represented by the formulae (24a) to (24x). Specifically, the following conjugated aromatic compounds represented by the formulae (III-1) to (III-6) are listed. Herein, in the following formulae, h and p represents the same meanings as defined above.

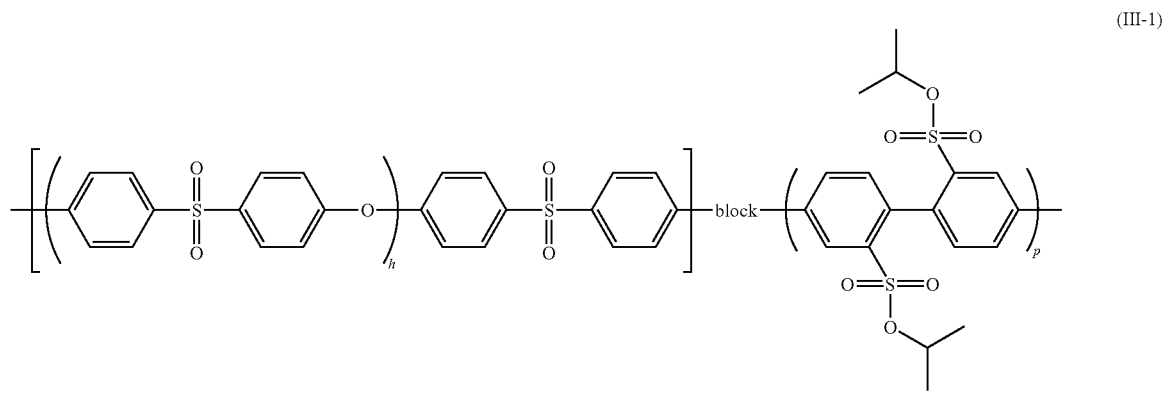

(III-1)

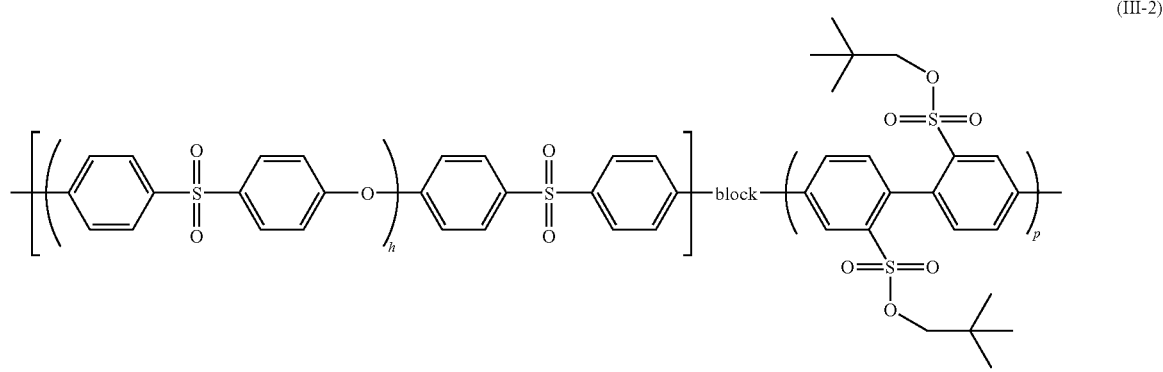

(III-2)

-continued

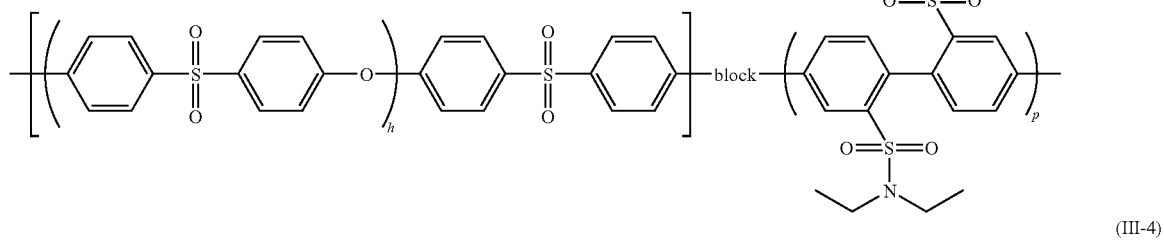

(III-3)

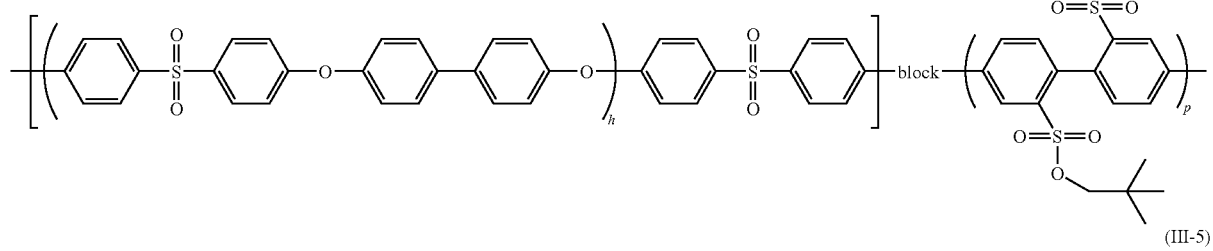

(III-4)

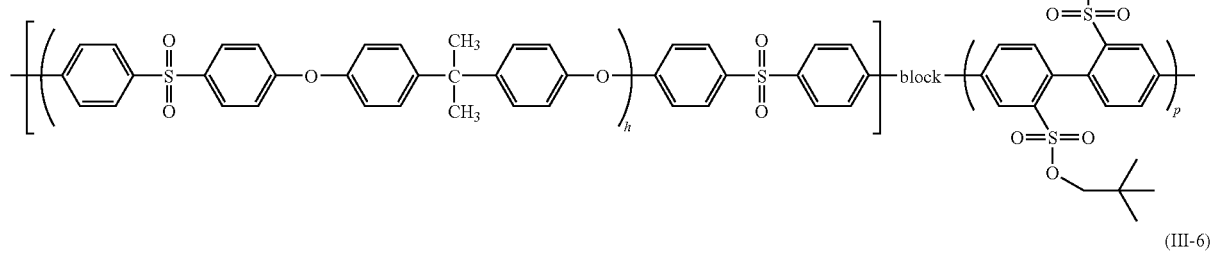

(III-5)

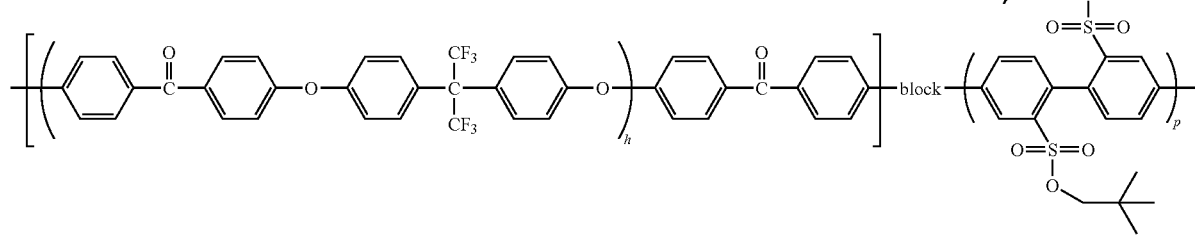

(III-6)

In a case where an aromatic compound (A) is reacted with an aromatic compound (B) being structurally different from the above-mentioned aromatic compound (A) and the aromatic compound (4) wherein n is 2 is used as the aromatic compound (A) and the aromatic compound (5) is used as the aromatic compound (B), a conjugated aromatic compound comprising the above-mentioned repeating unit represented by the formula (21) and the above-mentioned repeating unit represented by the following formula (22) is obtained. The weight average molecular weight thereof equivalent to polystyrene of the conjugated aromatic compound is usually 1,000 to 2,000,000. The amount of the repeating unit represented by the formula (21) in the conjugated aromatic compound is preferably 1% by weight or more and 99% by weight or less, and the amount of the repeating unit represented by the formula (22) is preferably 1% by weight or more and 99% by weight or less.

Examples of the conjugated aromatic compound comprising the repeating unit represented by the formula (21) and the repeating unit represented by the formula (22) include a conjugated aromatic compound comprising any one repeating unit of the above-mentioned repeating units represented by the formulae (21a) to (21d) and any one segment of the above-mentioned repeating units represented by the formulae (22a) to (22e). Specifically, the following conjugated aromatic compounds represented by the formulae (IV-1) to (IV-4) are listed.

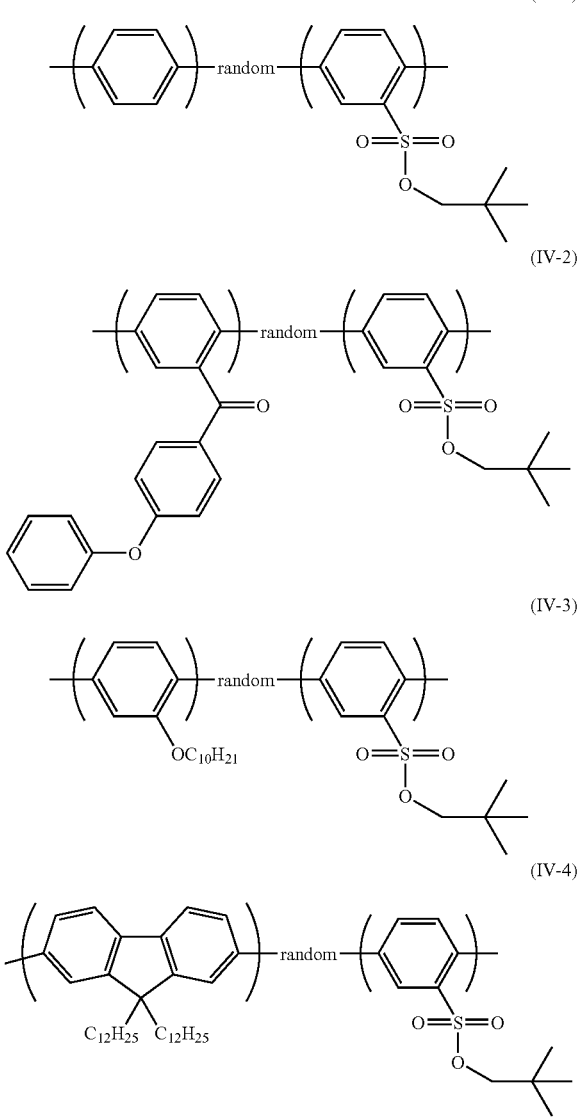

The content of each repeating unit in the conjugated aromatic compound comprising two or more kinds of the repeating unit can be adjusted by arbitrarily adjusting the used amount of the aromatic compounds used.

The conjugated aromatic compound comprising the repeating unit represented by the formula (22) or (23) can be used as a law material for synthesizing a polyelectrolyte for a polymer electrolyte fuel cell, and the preferable weight average molecular weight equivalent to polystyrene in such case is 2,000 to 1,000,000 and more preferable one is 3,000 to 800,000.

EXAMPLES

The present invention will be further illustrated by Examples in more detail below, but the present invention is not limited to these Examples.

When the obtained conjugated aromatic compound was not a polymer, it was analyzed according to gas chromatography internal standard method and the yield thereof was calculated from its result. When the obtained conjugated aromatic compound was a polymer, it was analyzed with gel permeation chromatography (hereinafter, simply referred to as GPC), of which analytical condition was as followed, and the weight-average molecular weight (Mw) and the number-average molecular weight (Mn) thereof were calculated from its result.

<Analytical Condition>
GPC measuring apparatus: CTO-10A (manufactured by Shimadzu Corporation)
Column: TSK-GEL (manufactured by Tosoh Corporation)
Column temperature: 40° C.
Eluent: N,N-dimethylacetamide containing lithium bromide (concentration of lithium bromide: 10 mmol/dm$^3$)
Flow rate: 0.5 mL/minute
Detection wavelength: 300 nm

Example 1-1

To a reaction container equipped with a dropping funnel, 8 g of 2,5-dibromopyridine and 90 ml of diethyl ether were added. The obtained solution was cooled at −70° C. and then, 21.37 mL of butyl lithium (1.58 M/hexane solution) was added dropwise thereto. The obtained mixture was stirred for 1 hour and 30 minutes and then, a solution obtained by dissolving 4.32 mL of trimethylchlorosilane in 6.2 mL of diethyl ether was added dropwise thereto. The obtained mixture was stirred for 2 hours and 40 minutes and then, 60 mL of water was added dropwise thereto at 0° C. The obtained mixture was stirred at room temperature overnight and then, 30 mL of diethyl ether was added thereto. The obtained solution was extracted three times with 30 mL of diethyl ether. The obtained organic layers were mixed and dried with magnesium sulfate. After removing magnesium sulfate by filtration, the filtrate was concentrated to obtain a crude product. The crude product was purified with silica gel column chromatography to obtain 5.96 g of 2-bromo-5-trimethylsilylpyridine. Purity: 90% (area percentage value obtained by gas chromatography analysis).

Example 1-2

To a reaction container equipped with a cooling apparatus, 0.75 g of tetrakis(triphenylphosphine)palladium, 1 g of 2-bromo-5-trimethylsilylpyridine obtained in the above-mentioned Example 1-1 and 25 mL of tetrahydrofuran were added. To the obtained mixture, 8.69 mL of 2-pyridyl zinc bromide (0.5 M/tetrahydrofuran solution) was added with stirring at room temperature. The obtained mixture was stirred at 50° C. for 8 hours to effect reaction. The reaction mixture was cooled until room temperature and then, 33 mL of 28% aqueous ammonia solution was added thereto. The obtained mixture was extracted three times with 50 mL of chloroform. The obtained organic layers were mixed and dried with magnesium sulfate. After removing magnesium sulfate by filtration, the filtrate was concentrated to obtain a crude product.

Example 1-3

The reaction was conducted according to the same manner as that of the above-mentioned Example 1-2, except that the used amounts of each reagent was doubled, to obtain a crude product. The obtained crude product was mixed with the crude product obtained in Example 1-2 and then, it was purified with silica gel column chromatography followed by further distillation to obtain 1.17 g of 5-trimethylsilyl-2,2′-bipyridine.

$^1$H-NMR (δ: ppm, CDCl$_3$ solvent, based on TMS)
8.77 (s, 1H), 8.69 (d, 1H), 8.42 (d, 1H), 8.36 (d, 1H), 7.93 (dd, 1H), 7.82 (m, 1H), 7.27-7.33 (m, 1H), 0.34 (s, 9H)

Example 2-1

To a reaction container equipped with a dropping funnel, 24 g of 2,5-dibromopyridine and 270 ml of diethyl ether were added. The obtained solution was cooled at −70° C. and then, 62.93 mL of butyl lithium (1.61 M/hexane solution) was added dropwise thereto. The obtained mixture was stirred for 2 hours and then, a solution obtained by dissolving 18.75 mL of cyclohexyldimethylchlorosilane in 18.6 mL of diethyl ether was added dropwise thereto. The obtained mixture was stirred for 4 hours and then, 140 mL of water was added dropwise thereto at 0° C. The obtained mixture was stirred at room temperature overnight and then, 40 mL of water and 150 mL of diethyl ether were added thereto. The obtained solution was extracted three times with 150 mL of diethyl ether. The obtained organic layers were mixed and dried with magnesium sulfate. After removing magnesium sulfate by filtration, the filtrate was concentrated to obtain a crude product. The crude product was purified with silica gel column chromatography to obtain 23 g of 2-bromo-5-cyclohexyldimethylsilylpyridine. Purity: 93% (area percentage value obtained by gas chromatography analysis).
$^1$H-NMR (δ: ppm, CDCl$_3$ solvent, based on TMS)
8.38 (s, 1H), 7.59 (dd, 1H), 7.45 (dd, 1H), 1.60-1.76 (c, 5H), 1.00-1.22 (c, 5H), 0.78-0.84 (m, 1H), 0.25 (s, 6H)<

Example 2-2

To a reaction container equipped with a cooling apparatus, 2.61 g of tetrakis(triphenylphosphine)palladium, 6.75 g of 2-bromo-5-cyclohexyldimethylsilylpyridine obtained in the above-mentioned Example 2-1 and 135 mL of tetrahydrofuran were added. To the obtained mixture, 45.26 mL of 2-pyridyl zinc bromide (0.5 M/tetrahydrofuran solution) was added with stirring at room temperature. The obtained mixture was stirred at 50° C. for 9 hours to effect reaction. The reaction mixture was cooled until room temperature and then, 200 mL of 28% aqueous ammonia solution was added thereto. The obtained mixture was extracted three times with 230 mL of chloroform. The obtained organic layers were mixed and dried with magnesium sulfate. After removing magnesium sulfate by filtration, the filtrate was concentrated to obtain a crude product. The crude product was purified with silica gel column chromatography followed by further distillation to obtain 4.04 g of 5-cyclohexyldimethylsilyl-2,2'-bipyridine.
$^1$H-NMR (δ: ppm, CDCl$_3$ solvent, based on TMS)
8.74 (s, 1H), 8.69 (d, 1H), 8.42 (d, 1H), 8.36 (d, 1H), 7.90 (dd, 1H), 7.81 (m, 1H), 7.27-7.32 (m, 1H), 1.68-1.71 (c, 5H), 1.07-1.20 (c, 5H), 0.79-0.90 (m, 1H), 0.34 (s, 6H)
$^{13}$C-NMR (δ: ppm, CDCl$_3$ solvent)
156.27, 156.04, 153.80, 149.16, 142.69, 136.82, 133.57, 123.66, 120.96, 120.11, 27.87, 27.26, 26.72, 25.54, −5.40

Example 3-1

To a reaction container equipped with a dropping funnel, 21.6 g of 2,5-dibromopyridine and 243 mL of diethyl ether were added. The obtained solution was cooled at −70° C. and then, 55.26 mL of butyl lithium (1.65 M/hexane solution) was added dropwise thereto. The obtained mixture was stirred for 3 hours and 10 minutes and then, a solution obtained by dissolving 20.96 mL of tert-butyldimethylsilyl trifluoromethanesulfonate in 16.7 mL of diethyl ether was added dropwise thereto. The obtained mixture was stirred for 17 hours and 55 minutes and then, 162 mL of water was added dropwise thereto at 0° C. The obtained mixture was stirred at room temperature for 30 minutes and then, 81 mL of ethyl acetate was added thereto. The obtained solution was extracted three times with 81 mL of ethyl acetate. The obtained organic layers were mixed and dried with magnesium sulfate. After removing magnesium sulfate by filtration, the filtrate was concentrated to obtain a crude product. The crude product was purified with silica gel column chromatography followed by further recrystallization with hexane to obtain 2.57 g of 2-bromo-5-tert-butyldimethylsilylpyridine. Purity: 98% (area percentage value obtained by gas chromatography analysis).
$^1$H-NMR (δ: ppm, CDCl$_3$ solvent, based on TMS)
8.40 (s, 1H), 7.62 (d, 1H), 7.46 (d, 1H), 0.88 (s, 9H), 0.29 (s, 6H)<

Example 3-2

To a reaction container equipped with a cooling apparatus, 0.64 g of tetrakis(triphenylphosphine)palladium, 1 g of 2-bromo-5-tert-butyldimethylsilylpyridine obtained in the above-mentioned Example 3-1 and 25 mL of tetrahydrofuran were added. To the obtained mixture, 7.35 mL of 2-pyridyl zinc bromide (0.5 M/tetrahydrofuran solution) was added with stirring at room temperature. The obtained mixture was stirred at 50° C. for 7 hours and 40 minutes to effect reaction. The reaction mixture was cooled until room temperature and then, 33 mL of 28% aqueous ammonia solution was added thereto. The obtained mixture was extracted three times with 50 mL of chloroform. The obtained organic layers were mixed and dried with magnesium sulfate. After removing magnesium sulfate by filtration, the filtrate was concentrated to obtain a crude product. The crude product was purified with silica gel column chromatography followed by further recrystallization with hexane to obtain 0.35 g of 5-tert-butyldimethylsilyl-2,2'-bipyridine.
$^1$H-NMR (δ: ppm, CDCl$_3$ solvent, based on TMS)
8.76 (s, 1H), 8.69 (d, 1H), 8.42 (d, 1H), 8.36 (d, 1H), 7.93 (dd, 1H), 7.83 (m, 1H), 7.26-7.34 (m, 1H), 0.91 (s, 9H), 0.34 (s, 6H)

Example 4-1

To a reaction container equipped with a dropping funnel, 24 g of 2,5-dibromopyridine and 270 mL of diethyl ether were added. The obtained solution was cooled at −70° C. and then, 61.4 mL of butyl lithium (1.65 M/hexane solution) was added dropwise thereto. The obtained mixture was stirred for 3 hours and 40 minutes and then, a solution obtained by dissolving 16.79 mL of dimethylphenylchlorosilane in 18.6 mL of diethyl ether was added dropwise thereto. The obtained mixture was stirred for 3 hours and then, 80 mL of water was added dropwise thereto at 0° C. The obtained mixture was stirred at room temperature overnight and then, 100 mL of water and 150 mL of ethyl acetate were added thereto. The obtained solution was extracted three times with 150 mL of ethyl acetate. The obtained organic layers were mixed and dried with magnesium sulfate. After removing magnesium sulfate by filtration, the filtrate was concentrated to obtain a crude product. The crude product was purified with silica gel column chromatography to obtain 25.1 g of 2-bromo-5-dimethylphenylsilylpyridine. Purity: 95% (area percentage value obtained by gas chromatography analysis).
$^1$H-NMR (δ: ppm, CDCl$_3$ solvent, based on TMS)
8.41 (s, 1H), 7.58 (dd, 1H), 7.36-7.50 (c, 6H), 0.58 (s, 6H)<

Example 4-2

To a reaction container equipped with a cooling apparatus, 2.37 g of tetrakis(triphenylphosphine)palladium, 6 g of 2-bromo-5-dimethylphenylsilylpyridine obtained in the above-mentioned Example 4-1 and 125 mL of tetrahydrofuran were added. To the obtained mixture, 41.06 mL of 2-pyridyl zinc bromide (0.5 M/tetrahydrofuran solution) was added with stirring at room temperature. The obtained mixture was stirred at 50° C. for 6 hours and 20 minutes to effect reaction. The reaction mixture was cooled until room temperature and then, 170 mL of 28% aqueous ammonia solution was added thereto. The obtained mixture was extracted three times with 200 mL of chloroform. The obtained organic layers were mixed and dried with magnesium sulfate. After removing magnesium sulfate by filtration, the filtrate was concentrated to obtain a crude product. The crude product was purified with silica gel column chromatography followed by further recrystallization with hexane to obtain 1.63 g of 5-dimethylphenylsilyl-2,2'-bipyridine.

$^1$H-NMR ($\delta$: ppm, CDCl$_3$ solvent, based on TMS)
8.77 (s, 1H), 8.68 (d, 1H), 8.41 (d, 1H), 8.38 (d, 1H), 7.92 (dd, 1H), 7.81 (m, 1H), 7.52-7.56 (c, 2H), 7.27-7.36 (c, 4H), 0.62 (s, 6H)<

Example 5-1

To a reaction container equipped with a dropping funnel, 8 g of 2,5-dibromopyridine and 90 mL of diethyl ether were added. The obtained solution was cooled at −70° C. and then, 20.47 mL of butyl lithium (1.65 M/hexane solution) was added dropwise thereto. The obtained mixture was stirred for 2 hours and then, a solution obtained by dissolving 7.08 mL of methyldiphenylchlorosilane in 6.2 mL of diethyl ether was added dropwise thereto. The obtained mixture was stirred for 5 hours and 50 minutes and then, 60 mL of water was added dropwise thereto at 0° C. The obtained mixture was stirred at room temperature overnight and then, 50 mL of ethyl acetate was added thereto. The obtained solution was extracted three times with 50 mL of ethyl acetate. The obtained organic layers were mixed and dried with magnesium sulfate. After removing magnesium sulfate by filtration, the filtrate was concentrated to obtain a crude product.

Example 5-2

The reaction was conducted according to the same manner as that of the above-mentioned Example 5-1, except that the used amounts of each reagent was trebled, to obtain a crude product. The obtained crude product was mixed with the crude product obtained in the above-mentioned Example 5-1 and then, and it was purified with silica gel column chromatography to obtain 36.1 g of 2-bromo-5-methyldiphenylsilylpyridine. Purity: 97% (area percentage value obtained by gas chromatography analysis).

$^1$H-NMR ($\delta$: ppm, CDCl$_3$ solvent, based on TMS)
8.41 (s, 1H), 7.34-7.60 (c, 12H), 0.86 (s, 3H)<

Example 5-3

To a reaction container equipped with a cooling apparatus, 2.28 g of tetrakis(triphenylphosphine)palladium, 7 g of 2-bromo-5-methyldiphenylsilylpyridine obtained in the above-mentioned Example 5-2 and 125 mL of tetrahydrofuran were added. To the obtained mixture, 39.51 mL of 2-pyridyl zinc bromide (0.5 M/tetrahydrofuran solution) was added with stirring at room temperature. The obtained mixture was stirred at 50° C. for 7 hours and 25 minutes to effect reaction. The reaction mixture was cooled until room temperature and then, 170 mL of 28% aqueous ammonia solution was added thereto. The obtained mixture was extracted three times with 200 mL of chloroform. The obtained organic layers were mixed and dried with magnesium sulfate. After removing magnesium sulfate by filtration, the filtrate was concentrated to obtain a crude product. The crude product was purified with silica gel column chromatography followed by further recrystallization with hexane to obtain 2.56 g of 5-methyldiphenylsilyl-2,2'-bipyridine.

$^1$H-NMR ($\delta$: ppm, CDCl$_3$ solvent, based on TMS)
8.75 (s, 1H), 8.69 (d, 1H), 8.36-8.43 (c, 2H), 7.93 (dd, 1H), 7.81 (m, 1H), 7.29-7.56 (c, 11H), 0.90 (s, 3H)<

Example 6-1

To a reaction container equipped with a dropping funnel, 8 g of 2,5-dibromopyridine and 90 mL of diethyl ether were added. The obtained solution was cooled at −70° C. and then, 20.47 mL of butyl lithium (1.65 M/hexane solution) was added dropwise thereto. The obtained mixture was stirred for 1 hour and 20 minutes and then, 9.96 g of triphenylchlorosilane was added thereto with a small amount and further 10 mL of diethyl ether was added thereto. The obtained mixture was stirred for 27 hours and 20 minutes and then, 60 mL of water was added dropwise thereto at 0° C. The obtained mixture was stirred at room temperature overnight and then, 60 mL of water and 100 mL of chloroform were added thereto. The obtained mixture was extracted three times with 100 mL of chloroform. The obtained organic layers were mixed and dried with magnesium sulfate. After removing magnesium sulfate by filtration, the filtrate was concentrated to obtain a crude product.

Example 6-2

The reaction was conducted according to the same manner as that of the above-mentioned Example 6-1, except that the used amounts of each reagent was increased 1.25-fold, to obtain a crude product. The obtained crude product was mixed with the crude product obtained in the above-mentioned Example 6-1 and then, and it was purified with silica gel column chromatography followed by further recrystallization with chloroform/hexane to obtain 19.01 g of 2-bromo-5-triphenylsilylpyridine.

$^1$H-NMR ($\delta$: ppm, CDCl$_3$ solvent, based on TMS)
8.46 (s, 1H), 7.65 (dd, 1H), 7.37-7.55 (c, 16H)
$^{13}$C-NMR ($\delta$: ppm, CDCl$_3$ solvent)
156.91, 145.93, 144.31, 136.16, 132.34, 130.16, 129.08, 128.18, 127.74

Example 6-3

To a reaction container equipped with a cooling apparatus, 2.50 g of tetrakis(triphenylphosphine)palladium, 9 g of 2-bromo-5-triphenylsilylpyridine obtained in the above-mentioned Example 6-2 and 125 mL of tetrahydrofuran were added. To the obtained mixture, 43.23 mL of 2-pyridyl zinc bromide (0.5 M/tetrahydrofuran solution) was added with stirring at room temperature. The obtained mixture was stirred at 50° C. for 7 hours and 40 minutes to effect reaction. The reaction mixture was cooled until room temperature and then, 170 mL of 28% aqueous ammonia solution was added thereto. The obtained mixture was extracted three times with 200 mL of chloroform. The obtained organic layers were mixed and dried with magnesium sulfate. After removing magnesium sulfate by filtration, the filtrate was concentrated to obtain a crude product. The crude product was purified with silica gel column chromatography followed by further recrystallization with diethyl ether to obtain 1.92 g of 5-methyltriphenylsilyl-2,2'-bipyridine.

$^1$H-NMR (δ: ppm, $CDCl_3$ solvent, based on TMS)
8.81 (s, 1H), 8.68 (d, 1H), 8.39-8.43 (c, 2H), 8.00 (dd, 1H), 7.80 (m, 1H), 7.49-7.61 (c, 6H), 7.36-7.46 (c, 9H), 7.24-7.32 (m, 1H)

$^{13}$C-NMR (δ: ppm, $CDCl_3$ solvent)
156.56, 155.79, 155.75, 149.01, 144.68, 136.56, 136.07, 132.83, 129.78, 129.64, 127.92, 123.65, 120.91, 120.10

Example 7

A solution containing a nickel complex was obtained by mixing 0.55 mg of bis(1,5-cyclooctadiene)nickel (O), 0.46 mg of 5-trimethylsilyl-2,2'-bipyridine and 4 mL of tetrahydrofuran. UV-Vis (tetrahydrofuran solvent) λ max 570 nm Example 8

To a glass reaction container equipped with a cooling apparatus, 15.3 mg of nickel bromide, 19.2 mg of 5-trimethylsilyl-2,2'-bipyridine and 91.6 mg of zinc powder were added in an atmosphere of nitrogen at room temperature. To the obtained mixture, 88.6 mg of 4-chlorotoluene and 5 mL of N-methyl-2-pyrrolidone were added. The obtained mixture was reacted at 70° C. for 2 hours to obtain a reaction mixture containing 4,4'-dimethylbiphenyl. The yield of 4,4'-dimethylbiphenyl was 56.5 mg.

Example 9

The reaction was conducted according to the same manner as that of Example 8, except that 24.9 mg of 5-cyclohexyldimethylsilyl-2,2'-bipyridine was used in place of 5-trimethylsilyl-2,2'-bipyridine, to obtain a reaction mixture containing 4,4'-dimethylbiphenyl. The yield of 4,4'-dimethylbiphenyl was 58.3 mg.

Comparative Example 1

The reaction was conducted according to the same manner as that of Example 8, except that 13.1 mg of 2,2'-bipyridine was used in place of 5-trimethylsilyl-2,2'-bipyridine, to obtain a reaction mixture containing 4,4'-dimethylbiphenyl. The yield of 4,4'-dimethylbiphenyl was 36.5 mg.

Example 10

To a glass reaction container equipped with a cooling apparatus, 15.3 mg of nickel bromide, 24.4 mg of 5-dimethylphenylsilyl-2,2'-bipyridine and 91.6 mg of zinc powder were added in an atmosphere of nitrogen at room temperature. To the obtained mixture, 88.6 mg of 2-chlorotoluene and 5 mL of N-methyl-2-pyrrolidone were added. The obtained mixture was reacted at 70° C. for 2 hours to obtain a reaction mixture containing 2,2'-dimethylbiphenyl. The yield of 2,2'-dimethylbiphenyl was 25.5 mg.

Example 11

The reaction was conducted according to the same manner as that of Example 10, except that 29.6 mg of 5-methyldiphenylsilyl-2,2'-bipyridine was used in place of 5-dimethylphenylsilyl-2,2'-bipyridine, to obtain a reaction mixture containing 2,2'-dimethylbiphenyl. The yield of 2,2'-dimethylbiphenyl was 36.5 mg.

Example 12

The reaction was conducted according to the same manner as that of Example 10, except that 34.8 mg of 5-triphenylsilyl-2,2'-bipyridine was used in place of 5-dimethylphenylsilyl-2,2'-bipyridine, to obtain a reaction mixture containing 2,2'-dimethylbiphenyl. The yield of 2,2'-dimethylbiphenyl was 34.6 mg.

Comparative Example 2

The reaction was conducted according to the same manner as that of Example 10, except that 13.1 mg of 2,2'-bipyridine was used in place of 5-dimethylphenylsilyl-2,2'-bipyridine, to obtain a reaction mixture containing 2,2'-dimethylbiphenyl. The yield of 2,2'-dimethylbiphenyl was 12.8 mg.

Example 13

To a glass reaction container equipped with a cooling apparatus, 15.3 mg of nickel bromide, 19.2 mg of 5-trimethylsilyl-2,2'-bipyridine and 91.6 mg of zinc powder were added in an atmosphere of nitrogen at room temperature. To the obtained mixture, 99.8 mg of 4-chloroanisole and 5 mL of N-methyl-2-pyrrolidone were added. The obtained mixture was reacted at 70° C. for 2 hours to obtain a reaction mixture containing 4,4'-dimethoxybiphenyl. The yield of 4,4'-dimethoxybiphenyl was 66.4 mg.

Example 14

To a glass reaction container equipped with a cooling apparatus, 15.3 mg of nickel bromide, 19.2 mg of 5-trimethylsilyl-2,2'-bipyridine and 91.6 mg of zinc powder were added in an atmosphere of nitrogen at room temperature. To the obtained mixture, 99.8 mg of 3-chloroanisole and 5 mL of N-methyl-2-pyrrolidone were added. The obtained mixture was reacted at 70° C. for 2 hours to obtain a reaction mixture containing 3,3'-dimethoxybiphenyl. The yield of 3,3'-dimethoxybiphenyl was 68.6 mg.

Example 15

To a glass reaction container equipped with a cooling apparatus, 15.3 mg of nickel bromide, 19.2 mg of 5-trimethylsilyl-2,2'-bipyridine and 91.6 mg of zinc powder were added in an atmosphere of nitrogen at room temperature. To the obtained mixture, 109.6 mg of 1-chloro-4-(methoxymethyl) benzene and 5 mL of N-methyl-2-pyrrolidone were added. The obtained mixture was reacted at 70° C. for 2 hours to obtain a reaction mixture containing 4,4'-bis(methoxymethyl)biphenyl. The yield of 4,4'-bis(methoxymethyl)biphenyl was 67.8 mg.

Example 16

To a glass reaction container equipped with a cooling apparatus, 15.3 mg of nickel bromide, 19.2 mg of 5-trimethylsilyl-2,2'-bipyridine and 91.6 mg of zinc powder were added in an atmosphere of nitrogen at room temperature. To the obtained mixture, 108.2 mg of 4-chloroacetophenone and 5 mL of N-methyl-2-pyrrolidone were added. The obtained mixture was reacted at 70° C. for 2 hours to obtain a reaction mixture containing 4,4'-diacetylbiphenyl. The yield of 4,4'-diacetylbiphenyl was 73.9 mg.

Example 17

To a glass reaction container equipped with a cooling apparatus, 15.3 mg of nickel bromide, 19.2 mg of 5-trimethylsilyl-2,2'-bipyridine and 91.6 mg of zinc powder were added in an atmosphere of nitrogen at room temperature. To the obtained mixture, 90.0 mg of 4-chlorophenol and 5 mL of N-methyl-2-pyrrolidone were added. The obtained mixture was reacted at 70° C. for 2 hours to obtain a reaction mixture containing 4,4'-dihydroxybiphenyl. The yield of 4,4'-dihydroxybiphenyl was 24.2 mg.

Example 18

The reaction was conducted according to the same manner as that of Example 17, except that 24.9 mg of 5-cyclohexyldimethylsilyl-2,2'-bipyridine was used in place of 5-trimethylsilyl-2,2'-bipyridine, to obtain a reaction mixture containing 4,4'-dihydroxybiphenyl. The yield of 4,4'-dihydroxybiphenyl was 37.2 mg.

Example 19

The reaction was conducted according to the same manner as that of Example 17, except that 24.4 mg of 5-dimethylphenylsilyl-2,2'-bipyridine was used in place of 5-trimethylsilyl-2,2'-bipyridine, to obtain a reaction mixture containing 4,4'-dihydroxybiphenyl. The yield of 4,4'-dihydroxybiphenyl was 22.3 mg.

Example 20

The reaction was conducted according to the same manner as that of Example 17, except that 29.6 mg of 5-methyldiphenylsilyl-2,2'-bipyridine was used in place of 5-trimethylsilyl-2,2'-bipyridine, to obtain a reaction mixture containing 4,4'-dihydroxybiphenyl. The yield of 4,4'-dihydroxybiphenyl was 22.3 mg.

Example 21

To a glass reaction container equipped with a cooling apparatus, 15.3 mg of nickel bromide, 19.2 mg of 5-trimethylsilyl-2,2'-bipyridine and 91.6 mg of zinc powder were added in an atmosphere of nitrogen at room temperature. To the obtained mixture, 80.2 mg of 2-chloropyrimidine and 5 mL of N-methyl-2-pyrrolidone were added. The obtained mixture was reacted at 70° C. for 2 hours to obtain a reaction mixture containing 2,2'-bipyrimidine. The yield of 2,2'-bipyrimidine was 7.9 mg.

Example 22

To a glass reaction container equipped with a cooling apparatus, 15.3 mg of nickel bromide, 19.2 mg of 5-trimethylsilyl-2,2'-bipyridine and 91.6 mg of zinc powder were added in an atmosphere of nitrogen at room temperature. To the obtained mixture, 114.1 mg of 2-bromothiophene and 5 mL of N-methyl-2-pyrrolidone were added. The obtained mixture was reacted at 70° C. for 2 hours to obtain a reaction mixture containing 2,2'-bithiophene. The yield of 2,2'-bithiophene was 34.9 mg.

Example 23

The reaction was conducted according to the same manner as that of Example 22, except that 24.9 mg of 5-cyclohexyldimethylsilyl-2,2'-bipyridine was used in place of 5-trimethylsilyl-2,2'-bipyridine, to obtain a reaction mixture containing 2,2'-bithiophene. The yield of 2,2'-bithiophene was 36.6 mg.

Example 24

The reaction was conducted according to the same manner as that of Example 22, except that 24.4 mg of 5-dimethylphenylsilyl-2,2'-bipyridine was used in place of 5-trimethylsilyl-2,2'-bipyridine, to obtain a reaction mixture containing 2,2'-bithiophene. The yield of 2,2'-bithiophene was 38.2 mg.

Example 25

The reaction was conducted according to the same manner as that of Example 22, except that 29.6 mg of 5-methyldiphenylsilyl-2,2'-bipyridine was used in place of 5-trimethylsilyl-2,2'-bipyridine, to obtain a reaction mixture containing 2,2'-bithiophene. The yield of 2,2'-bithiophene was 34.9 mg.

Example 26

The reaction was conducted according to the same manner as that of Example 22, except that 34.8 mg of 5-triphenylsilyl-2,2'-bipyridine was used in place of 5-trimethylsilyl-2,2'-bipyridine, to obtain a reaction mixture containing 2,2'-bithiophene. The yield of 2,2'-bithiophene was 36.6 mg.

Comparative Example 3

The reaction was conducted according to the same manner as that of Example 22, except that 13.1 mg of 2,2'-bipyridine was used in place of 5-trimethylsilyl-2,2'-bipyridine, to obtain a reaction mixture containing 2,2'-bithiophene. The yield of 2,2'-bithiophene was 24.9 mg.

Example 27

To a glass reaction container equipped with a cooling apparatus, 22.9 mg of nickel bromide, 28.8 mg of 5-trimethylsilyl-2,2'-bipyridine, 400.1 mg of di(2,2-dimethylpropyl) 4,4'-dichlorobiphenyl-2,2'-disulfonate, 91.6 mg of zinc powder and 5 mL of N-methyl-2-pyrrolidone were added in an atmosphere of nitrogen at room temperature. The obtained mixture was stirred at 70° C. for 4 hours to effect reaction and a reaction mixture containing a conjugated aromatic compound consisting of a repeating unit represented by the following formula (i)

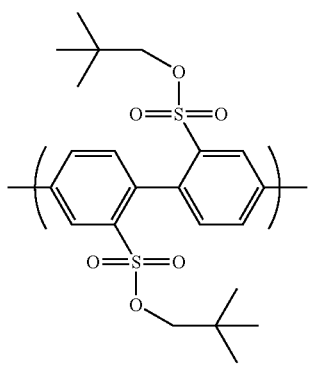

(i)

was obtained. Mw of the obtained conjugated aromatic compound was 184,200, and Mn thereof was 52,100.

Comparative Example 4

The reaction was conducted according to the same manner as that of Example 27, except that 19.7 mg of 2,2'-bipyridine was used in place of 5-trimethylsilyl-2,2'-bipyridine, to obtain a reaction mixture containing a conjugated aromatic compound consisting of a repeating unit represented by the above-mentioned formula (i). Mw of the obtained conjugated aromatic compound was 72,700, and Mn thereof was 25,300.

Example 28

To a glass reaction container equipped with a cooling apparatus, 15.3 mg of nickel bromide, 16.0 mg of 5-trimethylsilyl-2,2'-bipyridine, 394.1 mg of di(2,2-dimethylpropyl) 4,4'-dichlorobiphenyl-2,2'-disulfonate, 75.6 mg of zinc powder and 5 mL of N,N-dimethylacetamide were added in an atmosphere of nitrogen at room temperature. The obtained mixture was stirred at 70° C. for 4 hours to effect reaction and a reaction mixture containing a conjugated aromatic compound consisting of a repeating unit represented by the above-mentioned formula (i) was obtained. Mw of the obtained conjugated aromatic compound was 168,600, and Mn thereof was 53,000.

Example 29

The reaction was conducted according to the same manner as that of Example 28, except that 20.8 mg of 5-cyclohexyldimethylsilyl-2,2'-bipyridine was used in place of 5-trimethylsilyl-2,2'-bipyridine, to obtain a reaction mixture containing a conjugated aromatic compound consisting of a repeating unit represented by the above-mentioned formula (i). Mw of the obtained conjugated aromatic compound was 137,900, and Mn thereof was 43,000.

Example 30

The reaction was conducted according to the same manner as that of Example 28, except that 18.9 mg of 5-tert-butyldimethylsilyl-2,2'-bipyridine was used in place of 5-trimethylsilyl-2,2'-bipyridine, to obtain a reaction mixture containing a conjugated aromatic compound consisting of a repeating unit represented by the above-mentioned formula (1). Mw of the obtained conjugated aromatic compound was 139,400, and Mn thereof was 48,600.

Example 31

The reaction was conducted according to the same manner as that of Example 28, except that 20.3 mg of 5-dimethylphenylsilyl-2,2'-bipyridine was used in place of 5-trimethylsilyl-2,2'-bipyridine, to obtain a reaction mixture containing a conjugated aromatic compound consisting of a repeating unit represented by the above-mentioned formula (1). Mw of the obtained conjugated aromatic compound was 194,900, and Mn thereof was 64,500.

Example 32

The reaction was conducted according to the same manner as that of Example 28, except that 29.0 mg of 5-triphenylsilyl-2,2'-bipyridine was used in place of 5-trimethylsilyl-2,2'-bipyridine, to obtain a reaction mixture containing a conjugated aromatic compound consisting of a repeating unit represented by the above-mentioned formula (i). Mw of the obtained conjugated aromatic compound was 145,500, and Mn thereof was 48,200.

Comparative Example 5

The reaction was conducted according to the same manner as that of Example 28, except that 10.9 mg of 2,2'-bipyridine was used in place of 5-trimethylsilyl-2,2'-bipyridine, to obtain a reaction mixture containing a conjugated aromatic compound consisting of a repeating unit represented by the above-mentioned formula (i). Mw of the obtained conjugated aromatic compound was 131,200, and Mn thereof was 45,700.

Example 33

To a glass reaction container equipped with a cooling apparatus, 4.6 mg of nickel bromide, 5.8 mg of 5-trimethylsilyl-2,2'-bipyridine, 402.2 mg of di(2,2-dimethylpropyl) 4,4'-dichlorobiphenyl-2,2'-disulfonate, 94.3 mg of zinc powder and 5 mL of N,N-dimethylacetamide were added in an atmosphere of nitrogen at room temperature. The obtained mixture was stirred at 70° C. for 4 hours to effect reaction and a reaction mixture containing a conjugated aromatic compound consisting of a repeating unit represented by the above-mentioned formula (i) was obtained. Mw of the obtained conjugated aromatic compound was 12,600, and Mn thereof was 7,400.

Example 34

The reaction was conducted according to the same manner as that of Example 33, except that 7.3 mg of 5-dimethylphenylsilyl-2,2'-bipyridine was used in place of 5-trimethylsilyl-2,2'-bipyridine, to obtain a reaction mixture containing a conjugated aromatic compound consisting of a repeating unit represented by the above-mentioned formula (i). Mw of the obtained conjugated aromatic compound was 49,700, and Mn thereof was 20,200.

Example 35

To a glass reaction container equipped with a cooling apparatus, 30.6 mg of nickel bromide, 38.4 mg of 5-trimethylsilyl-2,2'-bipyridine, 462.5 mg of 2,7-dibromo-9,9-didodecyl-9H-fluorene, 91.6 mg of zinc powder, 3.5 mL of N,N-dimethylacetamide and 1.5 mL of toluene were added in an atmosphere of nitrogen at room temperature. The obtained mixture was stirred at 70° C. for 4 hours to effect reaction and a reaction mixture containing a conjugated aromatic compound consisting of a repeating unit represented by the following formula:

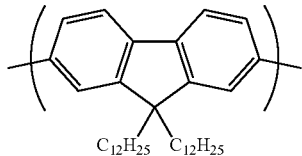

was obtained. Mw of the obtained conjugated aromatic compound was 97,400, and Mn thereof was 37,200.

Example 36

To a glass reaction container equipped with a cooling apparatus, 45.9 mg of nickel bromide, 57.5 mg of 5-trimethylsilyl-2,2'-bipyridine, 240.2 mg of 2,5-dichloro-4'-phenoxybenzophenone, 91.6 mg of zinc powder and 5 mL of N,N-dimethylacetamide were added in an atmosphere of nitrogen at room temperature. The obtained mixture was stirred at 70° C. for 4 hours to effect reaction and a reaction mixture containing a conjugated aromatic compound consisting of a repeating unit represented by the following formula:

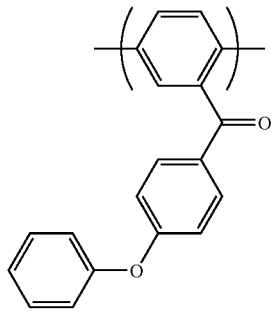

was obtained. Mw of the obtained conjugated aromatic compound was 85,700, and Mn thereof was 18,000.

Example 37

To a glass reaction container equipped with a cooling apparatus, 45.9 mg of nickel bromide, 57.5 mg of 5-trimethylsilyl-2,2'-bipyridine, 212.3 mg of 2,5-dichloro-1-decyloxybenzene, 91.6 mg of zinc powder and 3 mL of N-methyl-2-pyrrolidone were added in an atmosphere of nitrogen at room temperature. The obtained mixture was stirred at 70° C. for 4 hours to effect reaction and a reaction mixture containing a conjugated aromatic compound consisting of a repeating unit represented by the following formula:

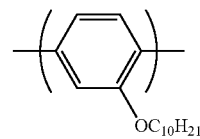

was obtained. Mw of the obtained conjugated aromatic compound was 13,800, and Mn thereof was 7,700.

Example 38

To a glass reaction container equipped with a cooling apparatus, 22.9 mg of nickel bromide, 28.8 mg of 5-trimethylsilyl-2,2'-bipyridine, 105.3 mg of zinc powder, a solution obtained by dissolving 402.2 mg of di(2,2-dimethylpropyl) 4,4'-dichlorobiphenyl-2,2'-disulfonate in 3 mL of N,N-dimethylacetamide, and a solution obtained by dissolving 71.1 mg of SUMIKA EXCEL PES 3100P represented by the following formula (ii):

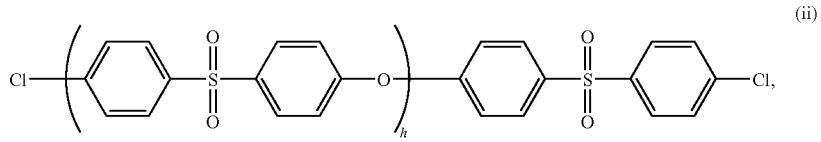

which was manufactured by Sumitomo Chemical Company, Limited; Mw 36,000 and Mn 18,000 which were measured by the above analytical conditions, in 2 mL of N,N-dimethylacetamide were added in an atmosphere of nitrogen at room temperature. The obtained mixture was stirred at 70° C. for 4 hours to effect reaction and a reaction mixture containing a conjugated aromatic compound comprising the repeating unit represented by the above-mentioned formula (i) and a segment represented by the following formula (iii):

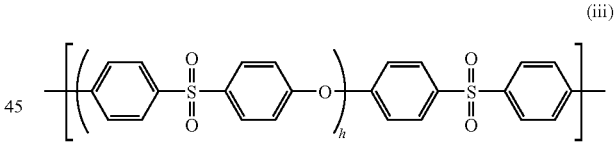

was obtained. Mw of the obtained conjugated aromatic compound was 359,800, and Mn thereof was 106,500.

Example 39

The reaction was conducted according to the same manner as that of Example 38, except that 36.6 mg of 5-dimethylphenylsilyl-2,2'-bipyridine was used in place of 5-trimethylsilyl-2,2'-bipyridine, to obtain a reaction mixture containing a conjugated aromatic compound comprising the repeating unit represented by the above-mentioned formula (i) and the segment represented by the above-mentioned formula (iii). Mw of the obtained conjugated aromatic compound was 371,900, and Mn thereof was 109,500.

Example 40

The reaction was conducted according to the same manner as that of Example 38, except that 206.3 mg of an aromatic compound represented by the following formula (iv):

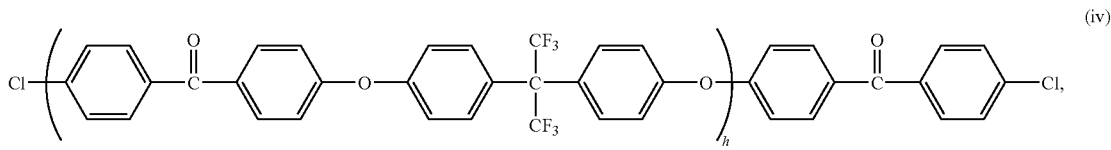

of which Mw was 5,900 and Mn was 3,900 which were measured by the above analytical conditions, was used in place of SUMIKA EXCEL PES 3100P represented by the formula (ii), to obtain a reaction mixture containing a conjugated aromatic compound comprising the repeating unit represented by the above-mentioned formula (i) and a segment represented by the following formula (v):

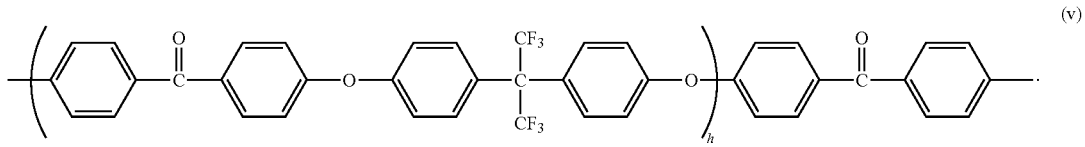

Mw of the obtained conjugated aromatic compound was 351,600, and Mn thereof was 94,500.

Example 41

The reaction was conducted according to the same manner as that of Example 40, except that 36.6 mg of 5-dimethylphenylsilyl-2,2'-bipyridine was used in place of 5-trimethylsilyl-2,2'-bipyridine, to obtain a reaction mixture containing a conjugated aromatic compound comprising the repeating unit represented by the above-mentioned formula (i) and the segment represented by the above-mentioned formula (v). Mw of the obtained conjugated aromatic compound was 372,100, and Mn thereof was 97,200.

INDUSTRIAL APPLICABILITY

The present novel bipyridine compound can be derived to a novel transition metal complex by contacting it with a compound of a transition metal belonging to Group 9, 10 or 11 and a conjugated aromatic compound can be produced more advantageously using the transition metal complex.

The invention claimed is:

1. A bipyridine compound represented by the formula (1):

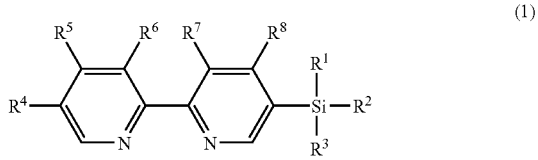

wherein $R^1$, $R^2$ and $R^3$ each independently represent a C1-C10 alkyl group which may be substituted, a C1-C5 alkoxy group which may be substituted or a C6-C10 aryl group which may be substituted, and $R^4$, $R^5$, $R^6$, $R^7$ and $R^8$ each independently represent a hydrogen atom or a C1-C3 alkyl group which may be substituted.

2. The bipyridine compound according to claim 1, wherein $R^1$, $R^2$ and $R^3$ each independently represent a methyl group, an ethyl group, an n-propyl group, an isopropyl group, a tert-butyl group, a cyclohexyl group, a benzyl group, a phenyl group, a 4-methylphenyl group, a methoxy group or an ethoxy group.

3. The bipyridine compound according to claim 1, wherein $R^1$, $R^2$ and $R^3$ are methyl groups.

4. The bipyridine compound according to claim 1, wherein $R^1$ is a methyl group, and $R^2$ and $R^3$ are phenyl groups.

5. The bipyridine compound according to claim 1, wherein $R^1$ and $R^2$ are methyl groups and $R^3$ is a phenyl group.

6. The bipyridine compound according to claim 1, wherein $R^1$ and $R^2$ are methyl groups and $R^3$ is a cyclohexyl group.

7. The bipyridine compound according to claim 1, wherein $R^1$ and $R^2$ are methyl groups and $R^3$ is a tert-butyl group.

8. The bipyridine compound according to claim 1, wherein $R^1$, $R^2$ and $R^3$ are phenyl groups.

9. The bipyridine compound according to claim 1, wherein $R^4$, $R^5$, $R^6$, $R^7$ and $R^8$ are hydrogen atoms.

10. A process for obtaining a transition metal complex comprising contacting a bipyridine compound represented by the formula (1):

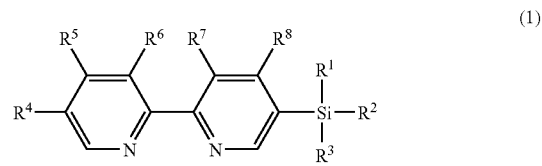

wherein $R^1$, $R^2$ and $R^3$ each independently represent a C1-C10 alkyl group which may be substituted, a C1-C5 alkoxy group which may be substituted or a C6-C10 aryl group which may be substituted, and $R^4$, $R^5$, $R^6$, $R^7$ and $R^8$ each independently represent a hydrogen atom or a C1-C3 alkyl group which may be substituted, with a compound of a transition metal belonging to Group 9, 10 or 11.

11. The process according to claim 10, which is obtained by contacting the bipyridine compound represented by the formula (1) with a compound of a transition metal belonging to Group 10.

12. The process according to claim 11, wherein the compound of a transition metal belonging to Group 10 is a nickel compound.

13. The process according to claim 10, wherein $R^1$, $R^2$ and $R^3$ each independently represent a methyl group, an ethyl group, an n-propyl group, an isopropyl group, a tert-butyl group, a cyclohexyl group, a benzyl group, a phenyl group, a 4-methylphenyl group, a methoxy group or an ethoxy group.

14. The process according to claim 10, wherein $R^1$, $R^2$ and $R^3$ are methyl groups.

15. The process according to claim 10, wherein $R^1$ is a methyl group and $R^2$ and $R^3$ are phenyl groups.

16. The process according to claim 10, wherein $R^1$ and $R^2$ are methyl groups and $R^3$ is a phenyl group.

17. The process according to claim 10, wherein $R^1$ and $R^2$ are methyl groups and $R^3$ is a cyclohexyl group.

18. The process according to claim 10, wherein $R^1$ and $R^2$ are methyl groups and $R^3$ is a tert-butyl group.

19. The process according to claim 1, wherein $R^1$, $R^2$ and $R^3$ are phenyl groups.

20. The process according to claim 10, wherein $R^4$, $R^5$, $R^6$, $R^7$ and $R^8$ are hydrogen atoms.

21. A method for production of a bipyridine compound represented by the formula (1):

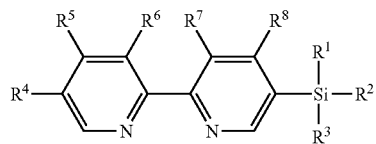

(1)

wherein $R^1$, $R^2$ and $R^3$ each independently represent a C1-C10 alkyl group which may be substituted, a C1-C5 alkoxy group which may be substituted or a C6-C10 aryl group which may be substituted, and $R^4$, $R^5$, $R^6$, $R^7$ and $R^8$ each independently represent a hydrogen atom or a C1-C3 alkyl group which may be substituted, which comprises reacting a pyridine compound represented by the formula (2):

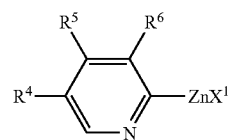

(2)

wherein $R^4$, $R^5$ and $R^6$ are the same as defined above, and X' represents a halogen atom, with a pyridine compound represented by the formula (3):

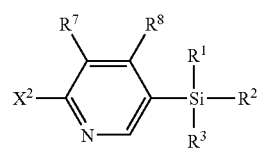

(3)

wherein $R^1$, $R^2$, $R^3$, $R^7$ and $R^8$ are the same as defined above, and $X^2$ represents a halogen atom, a trifluoromethanesulfonyloxy group, a p-toluenesulfonyloxy group or a methanesulfonyloxy group, in the presence of a palladium catalyst.

* * * * *